(12) United States Patent
Shen et al.

(10) Patent No.: US 12,318,263 B2
(45) Date of Patent: Jun. 3, 2025

(54) MANDIBULAR POSITIONING FACIAL RETROGNATHISM ORTHODONTIC SYSTEM AND DESIGN METHOD THEREOF

(71) Applicants: Shanghai Smartee Denti-Technology Co., Ltd., Shanghai (CN); Gang Shen, Shanghai (CN); Taikang Bybo Dental Group Co., Ltd., Guangdong (CN)

(72) Inventors: Gang Shen, Shanghai (CN); Junfeng Yao, Shanghai (CN)

(73) Assignee: SHANGHAI SMARTEE DENTI-TECHNOLOGY CO., LTD., Shanghai (CN)

( * ) Notice: Subject to any disclaimer, the term of this patent is extended or adjusted under 35 U.S.C. 154(b) by 473 days.

(21) Appl. No.: 17/655,377

(22) Filed: Mar. 18, 2022

(65) Prior Publication Data

US 2022/0202538 A1 Jun. 30, 2022

Related U.S. Application Data

(63) Continuation of application No. PCT/CN2019/128223, filed on Dec. 25, 2019.

(30) Foreign Application Priority Data

Sep. 20, 2019 (CN) .......................... 201910897878.2

(51) Int. Cl.
*A61C 7/36* (2006.01)
*A61C 7/06* (2006.01)
(Continued)

(52) U.S. Cl.
CPC ............... *A61C 7/36* (2013.01); *A61C 7/06* (2013.01); *A61C 7/08* (2013.01); *A61C 7/10* (2013.01)

(58) Field of Classification Search
CPC .... A61C 7/36; A61C 7/06; A61C 7/08; A61C 7/10; A61C 7/00
(Continued)

(56) References Cited

U.S. PATENT DOCUMENTS

| 6,702,575 B2 | 3/2004 | Hilliard |
| 2007/0092850 A1 | 4/2007 | Kaza |

(Continued)

FOREIGN PATENT DOCUMENTS

| AU | 2005201456 B2 | 8/2007 |
| CA | 2827760 A1 | 3/2015 |

(Continued)

OTHER PUBLICATIONS

Shanghai Smartee Denti-Technology Co., Ltd., et al., Communication pursuant to Article 94(3) EPC, EP 19945581.7, Jun. 27, 2023, 7 pgs.

(Continued)

*Primary Examiner* — Ralph A Lewis
*Assistant Examiner* — Mirayda A Aponte
(74) *Attorney, Agent, or Firm* — Nicholas Mesiti, Esq.; Heslin Rothenberg Farley & Mesiti P.C.

(57) ABSTRACT

A mandibular positioning facial retrognathism orthodontic system and a design method thereof are disclosed. The orthodontic system includes a maxillary shell-like dental appliance having a shell-like body, a protrusion portion protruding toward an opposite jaw is disposed at a posterior area corresponding to the shell-like body, a traction portion is disposed at a labial side of the shell-like body, and a retaining portion configured for fastening with a retaining attachment is disposed at the posterior area corresponding to the shell-like body. The protrusion portion is engaged with the posterior area of a mandibular for occlusal reconstruction, so that mandibular incisors are aligned with maxillary (Continued)

incisors. The design method is a design method for the mandibular positioning facial retrognathism orthodontic system, which can provide a treatment-specific orthodontic system, thereby achieving treatment of mandibular positioning facial retrognathism.

11 Claims, 11 Drawing Sheets

(51) Int. Cl.
 *A61C 7/08* (2006.01)
 *A61C 7/10* (2006.01)
(58) Field of Classification Search
 USPC .......................................................... 433/19
 See application file for complete search history.

(56) References Cited

U.S. PATENT DOCUMENTS

| | | |
|---|---|---|
| 2007/0283967 A1 | 12/2007 | Bailey |
| 2014/0120490 A1 | 5/2014 | Borovinskih et al. |

FOREIGN PATENT DOCUMENTS

| | | |
|---|---|---|
| CN | 102068316 A | 5/2011 |
| CN | 102805666 A | 12/2012 |
| CN | 203885643 U | 10/2014 |
| CN | 104434323 A | 3/2015 |
| CN | 204581556 U | 8/2015 |
| CN | 204951187 U | 1/2016 |
| CN | 106137416 A | 11/2016 |
| CN | 106137417 A | 11/2016 |
| CN | 206044762 U | 3/2017 |
| CN | 106687067 A | 5/2017 |
| CN | 106691608 A | 5/2017 |
| CN | 107088101 A | 8/2017 |
| CN | 107106261 A | 8/2017 |
| CN | 206403873 U | 8/2017 |
| CN | 107802360 A | 3/2018 |
| CN | 207306735 U | 5/2018 |
| CN | 207721906 U | 8/2018 |
| CN | 108498192 A | 9/2018 |
| CN | 108697490 A | 10/2018 |
| CN | 109394356 A | 3/2019 |
| CN | 109567962 A | 4/2019 |
| CN | 208677615 U | 4/2019 |
| CN | 208725922 U | 4/2019 |
| CN | 208784953 U | 4/2019 |
| CN | 109893263 A | 6/2019 |
| CN | 208942431 U | 6/2019 |
| CN | 209059487 U | 7/2019 |
| CN | 110123464 A | 8/2019 |
| CN | 110179560 A | 8/2019 |
| CN | 110584805 A | 12/2019 |
| EP | 1143872 B2 | 2/2019 |
| JP | H11155884 A | 6/1999 |
| JP | 2008054989 A | 3/2008 |
| WO | 2010087824 A1 | 8/2010 |
| WO | 2015054726 A1 | 4/2015 |
| WO | 2017007964 A1 | 1/2017 |
| WO | 2017106896 A1 | 6/2017 |
| WO | 2017154641 A1 | 9/2017 |
| WO | WO-2019043097 A1 * | 3/2019 ............... A61C 7/08 |

OTHER PUBLICATIONS

Shen, et al., International Search Report with English translation, PCT/CN2019/128223, Jun. 10, 2020, 6pgs.
Shanghai Smartee Denti-Technology Co., Ltd., CN First Office Action with English translation, CN 2019108978782, Dec. 16, 2020, 19pgs.
Shanghai Smartee Denti-Technology Co., Ltd., CN Second Office Action with English translation, CN 2019108978782, Jun. 31, 2021, 28pgs.
Shanghai Smartee Denti-Technology Co., Ltd., CN First Office Action with English translation, CN 2019108936559, Jan. 5, 2021, 18pgs.
Shanghai Smartee Denti-Technology Co., Ltd., CN Second Office Action with English translation, CN 2019108936559, Aug. 3, 2021, 16pgs.
Zhang, et al., pp. 650-653 of Modern Practical Stomatology Part II, Jilin Science and Technology Press, May 31, 2016, 6pgs.
Shanghai Smartee Denti-Technology Co., Ltd et al., Extended European Search Report, EP 19945581.7, Sep. 8, 2022, 8 pgs.

* cited by examiner

MANDIBULAR POSITIONING FACIAL RETROGNATHISM ORTHODONTIC SYSTEM AND DESIGN METHOD THEREOF

CROSS REFERENCE TO RELATED APPLICATIONS

The present application is a continuation of International Application No. PCT/CN2019/128223, filed on Dec. 25, 2019, which claims priority of Chinese Patent Application No. 201910897878.2, filed on Sep. 20, 2019 and entitled "MANDIBULAR POSITIONING FACIAL RETROGNATHISM ORTHODONTIC SYSTEM AND DESIGN METHOD THEREOF", each of the aforementioned applications is incorporated herein by reference in its entirety.

TECHNICAL FIELD

Some embodiments of the present disclosure relate to the technical field of medical devices, specifically to dental orthodontic design technologies, and more specifically to a mandibular positioning facial retrognathism orthodontic system and design method thereof.

BACKGROUND

Malocclusion refers to, during the growth stage of children, caused by congenital genetic factors or acquired environmental factors such as diseases, bad oral habits, and tooth replacement disorders, or caused by trauma, periodontal diseases or other reasons after the growth stage, misalignment of teeth, abnormal occlusal relationship between upper and lower dental arches, abnormal size, morphology, and position of the jaw bone, a facial deformity, or the like. Formation factors and mechanisms of malocclusion are complex, and its occurrence process may be caused by a single factor and a single mechanism, or may be caused by a plurality of factors or a plurality of mechanisms. From the time of formation of malocclusion, etiology of malocclusion may be divided into two categories: congenital factors and acquired factors. However based on the perspective of the mechanism of individual malocclusion, the etiology of malocclusion may be divided into innate genetic factors and external environmental factors.

Mandibular positioning facial retrognathism is mainly caused by inertial protrusion of the lower jaw, where the upper jaw is slightly hypoplastic, and morphology of the lower jaw is better and into a flat square shape. At the early stage of permanent dentition, anterior teeth deeply undergo a reverse overbite and a reverse overjet, and molars and canines are in a mesial relationship. That is, posterior teeth are completely mesial, the canines are mesial, and maxillary canines are aligned with mandibular canines.

An important clinical feature of the mandibular positioning facial retrognathism is that the lower jaw may be forced to retract until make upper and lower anterior incisors be aligned, and posterior tooth opening is caused by a deep curve of Spee of the lower jaw.

Angel's class III malocclusion is due to an imbalance of the mesial and distal relationship between upper and lower jaw bones and the dental arch, where the lower jaw and the lower dental arch are in a mesial position, and molars are in a mesial relationship. If the lower jaw is moved forward by ¼ of a molar or a half of a premolar, that is, when the mesial buccal cusp of the first permanent molar of the upper jaw is opposite to the distal buccal cusp of the first permanent molar of the lower jaw, it is referred to as a mild mesial malocclusion relationship or an initial mesial malocclusion. If the lower jaw or the lower dental arch is in a more mesial position, so that the mesial buccal cusp of the first permanent molar of the upper jaw is located between the first permanent molar of the upper jaw and the mandibular second permanent molar during occlusion, it is referred to as complete mesial malocclusion. The class III malocclusion may be manifested as anterior opposing jaw, underbite or jaw opening, maxillary retraction, or mandibular protrusion. The class III malocclusion may be manifested as anterior opposing jaw, underbite or jaw opening, maxillary retraction, or mandibular protrusion. A facial change shown in some cases is that the face is of a facial retrognathism.

The facial retrognathism may be divided into a dento-alveolar, a mandibular positioning, and skeletal categories. Clinical manifestations of the dento-alveolar facial retrognathism are that a slight concave surface is observed when viewed from a side, no collapse is observed in the paranasal area when viewed from the front, mandibular steepness is normal, the reverse overjet of anterior teeth is relatively small, and molars are slightly in a mesial relationship, which is mainly caused by local factors of dento-alveolar, where the maxillary bone is normal, and the morphology of the lower jaw is normal and is in the shape of a rectangle.

Clinical manifestations of the mandibular positioning facial retrognathism are that an obvious concave surface is observed when viewed from a side, the mandibular steepness is normal, the reverse overjet of anterior teeth is large, the reverse overbite is deep, the lower jaw is retracted until the upper and lower jaws in the anterior area are aligned, molars are in a mesial relationship, which is mainly caused by inertial protrusion of the lower jaw, the upper jaw is underdeveloped, the underbite is mainly caused by mandibular positioning factors, the maxillary bone is slightly retracted, and the morphology of the lower jaw is normal and is in the shape of a rectangle.

The skeletal categories facial retrognathism is divided into three types: maxillary originated, mandibular originated, and maxillo-mandibular originated. Clinical manifestations of the maxillary originated are that an obvious concave surface is observed when viewed from a side, no collapse is observed in the paranasal area when viewed from the front, the mandibular steepness is normal, the reverse overjet of anterior teeth is relatively large, the posterior area overjet is relatively small, and the molars are in a mesial relationship, which is mainly caused by underdevelopment of the upper jaw in all sides, the dento-alveolar and a basal bone are in reverse compensation, to form a depression at the transition between the alveolus and the basal bone, the upper jaw is underdeveloped, and the morphology of the lower jaw is normal and is in the shape of a rectangle. Clinical manifestations of the mandibular originated are that the upper jaw is relatively normal, plane steepness of the lower jaw is relatively large, a concave surface is obvious, the reverse overjet of anterior teeth is relatively small, and the posterior area is of the reverse overjet, the molars are in a mesial relationship, which is mainly caused by overdevelopment of the lower jaw in all sides, the dento-alveolar and the jaw bone are in reverse compensation, resulting in that lower anterior teeth are upright or tongue tilted, the maxillary bone is slightly retracted, the morphology of the lower jaw is poor and in the shape of a thick triangle, the shallow concave converges is retracted, and the deep concave protrudes forward. Clinical manifestations of the maxillo-mandibular originated are that the upper jaw is retracted and the lower jaw protrudes when viewed from a side, a depression is observed in the paranasal area when viewed from the front, the reverse overjet of anterior teeth is relatively small, the overjet of the posterior area is obvious, the molars are in a mesial relationship, which is mainly caused by underdevelopment of the upper jaw in all sides and overdevelopment of the lower jaw in all sides, the maxillary bone is obviously retracted, the morphology of the lower jaw is poor and in the shape of a thick triangle, the shallow concave is retracted, and the deep concave protrudes forward.

SUMMARY

An objective of some embodiments of the present disclosure is to provide a mandibular positioning facial retrognathism orthodontic system, by making a shell-like dental appliance and an auxiliary device engage, and dividing different orthodontic stages, thereby gradually realizing the orthodontic of mandibular positioning facial retrognathism, and improving the wearing comfort of patients without affecting the orthodontic effect.

The present disclosure further provides a design method for a mandibular positioning facial retrognathism orthodontic system. A Mandibular positioning facial retrognathism orthodontic system is provided according to an actual orthodontic stage, and according to different orthodontic stages, different shell-like dental appliances are designed to be engaged with an auxiliary device, to achieve a final orthodontic effect.

Technical solutions provided in some embodiments of the present disclosure are as follows.

A mandibular positioning facial retrognathism orthodontic system is provided, including a maxillary shell-like dental appliance having a shell-like body, here the shell-like body is provided with a plurality of cavities for accommodating teeth, a protrusion portion protruding toward an opposite jaw is disposed at a posterior area corresponding to the shell-like body, a traction portion is disposed at a labial side of an outer surface of the shell-like body in contact with the teeth, and a retaining portion configured for fastening with a retaining attachment is disposed at the posterior area corresponding to the shell-like body;

The protrusion portion is engaged with the posterior area of a mandibular for occlusal reconstruction, so that mandibular incisors are aligned with maxillary incisors; the traction portion is engaged with a maxillary for extramaxillary reverse traction for orthodontic remolding of jaw bones.

A shape of an anterior area of the maxillary shell-like dental appliance gradually changes, so that corresponding teeth are gradually aligned from an initial position to a target orthodontic position, and a height of the protrusion portion disposed on the maxillary shell-like dental appliance gradually decreases with the change of the shape of the anterior area of the maxillary shell-like dental appliance.

Further, in some embodiments, the mandibular positioning facial retrognathism orthodontic system further includes a mandibular shell-like dental appliance, here the mandibular shell-like dental appliance includes a shell-like body provided with a plurality of cavities for accommodating mandibular teeth, and a shape of an anterior area of the mandibular shell-like dental appliance gradually changes during orthodontic remolding of the jaw bones, so that corresponding teeth are gradually depressed from an initial position to a target orthodontic position.

Further, in some embodiments, the mandibular positioning facial retrognathism orthodontic system further includes a first intermaxillary traction member disposed on the maxillary shell-like dental appliance and a second intermaxillary traction member disposed on the mandibular shell-like dental appliance, and after orthodontic remolding of the jaw bones, the first intermaxillary traction member and the second intermaxillary traction member are connected by an elastic member, so that an occlusal relationship between maxillary and mandibular teeth is adjusted.

Further, in some embodiments, when the jaw opening is relatively large, the mandibular positioning facial retrognathism orthodontic system further includes a first interactive traction member disposed on the maxillary shell-like dental appliance and a second interactive traction member disposed on the mandibular shell-like dental appliance, and after orthodontic remolding of the jaw bones and before adjusting the occlusal relationship between the maxillary and mandibular teeth, the first interactive traction member and the second interactive traction member are connected by an elastic member, so that posterior teeth are released from jaw opening.

Further, in some embodiments, a shape of a posterior area of the mandibular shell-like dental appliance gradually changes, so that corresponding teeth are gradually adducted from the initial position to the target orthodontic position.

Further, in some embodiments, the mandibular positioning facial retrognathism orthodontic system further includes: an intramaxillary traction member disposed on the mandibular shell-like dental appliance and an implant anchorage member disposed on a mandibular alveolar bone, and after orthodontic remolding of the jaw bones, the implant anchorage member and the intramaxillary traction member are connected by an elastic member, so that the occlusal relationship between the maxillary and mandibular teeth is adjusted.

Further, in some embodiments, a part of the protrusion portion facing an opposing jaw dentition occlusal surface is provided with a friction portion configured to provide a stable contact between upper and lower jaws during occlusal reconstruction.

Further, in some embodiments, the friction portion is of one, two or a combination of more than two of a structure for concave-convex engagement with an opposing tooth occlusal surface, a structure for occlusal engagement with the opposing tooth occlusal surface, a structure with a matte surface, a structure with bumps, a structure with a hollowed surface, or a structure with a porous surface.

Further, in some embodiments, the retaining portion has at least two outer surfaces, and each of the outer surfaces of the retaining portion is disposed at a specific angle relative to a labial side of the maxillary shell-like dental appliance.

Further, in some embodiments, the retaining portion includes a first curved surface and a second curved surface, the first curved surface and the second curved surface jointly define a retaining attachment accommodating space having an open end and a closed end, bending directions of the first curved surface and the second curved surface are the same, and curvatures of the first curved surface and the second curved surface are different.

Further, in some embodiments, an included angle formed between a tangential direction at any point on the first curved surface and a tangential direction at any point on the second curved surface is an acute angle.

Further, some embodiments of the present disclosure further provide a design method for a mandibular positioning facial retrognathism orthodontic system, including following steps.

Designing a maxillary shell-like dental appliance having a shell-like body, and adjusting a shape of an anterior area of the maxillary shell-like dental appliance, so that teeth corresponding to the anterior area are gradually aligned from an initial position to a target orthodontic position.

Disposing a protrusion portion protruding towards an opposite jaw at a posterior area corresponding to the maxillary shell-like dental appliance. Here the protrusion portion is engaged with a mandibular posterior area to occlusal reconstruction, so that mandibular incisors are aligned with maxillary incisors.

Providing a retaining portion on a part of the protrusion portion wrapping corresponding teeth, here the retaining portion is configured for fastening with a retaining attachment disposed on the teeth.

Disposing a traction portion on a labial side on which an outer surface of the maxillary shell-like dental appliance is in contact with teeth. Here the traction portion is engaged with a maxillary for extramaxillary reverse traction for orthodontic remolding of jaw bones.

Herein a height of the protrusion portion disposed on the maxillary shell-like dental appliance gradually decreases with a change of the shape of the anterior area of the maxillary shell-like dental appliance.

Further, in some embodiments, the design method further includes: designing a mandibular shell-like dental appliance. Here a shape of an anterior area of the mandibular shell-like dental appliance gradually changes during orthodontic remolding of the jaw bones, so that corresponding teeth are gradually depressed from the initial position to the target orthodontic position.

Further, in some embodiments, the design method further includes: disposing a first intermaxillary traction member on the maxillary shell-like dental appliance and disposing a second intermaxillary traction member on the mandibular shell-like dental appliance. Here after orthodontic remolding of the jaw bones, the first intermaxillary traction member and the second intermaxillary traction member are connected, so that an occlusal relationship between maxillary and mandibular teeth is adjusted.

Further, in some embodiments, the design method further includes: disposing a first interactive traction member on the maxillary shell-like dental appliance and disposing a second interactive traction member on the mandibular shell-like dental appliance. Here after orthodontic remolding of the jaw bones and before adjusting of the occlusal relationship between the maxillary and mandibular teeth, the first interactive traction member and the second interactive traction member are connected, so that posterior teeth are released from jaw opening.

Further, in some embodiments, a shape of a posterior area of the mandibular shell-like dental appliance gradually changes, so that corresponding teeth are gradually adducted from the initial position to the target orthodontic position.

Further, in some embodiments, the design method further includes: an intramaxillary traction member disposed on the mandibular shell-like dental appliance and an implant anchorage member disposed on a mandibular alveolar bone. Here after orthodontic remolding of the jaw bones, the implant anchorage member and the intramaxillary traction member are connected by an elastic member, so that the occlusal relationship between the maxillary and mandibular teeth is adjusted.

The mandibular positioning facial retrognathism orthodontic system and a design method thereof of the present disclosure have at least following advantages.

1) The mandibular positioning facial retrognathism overall orthodontic system provided by some embodiments of the present disclosure, by making the protrusion portion and the mandibular posterior area to engage for occlusal reconstruction, so that mandibular incisors are aligned with maxillary incisors. The traction portion is engaged with a maxillary for extramaxillary reverse traction for remodeling and occlusal reconstruction of the jaw bones; and the shape of the anterior area of the maxillary shell-like dental appliance gradually changes, so that corresponding teeth are gradually aligned from the initial position to the target orthodontic position, and the height of the protrusion portion disposed on the maxillary shell-like dental appliance gradually decreases with the change of the shape of the anterior area of the maxillary shell-like dental appliance, to achieve orthopedics and tooth orthodontic.

2) After orthopedic reconstruction of the jaw bones, that is, an improvement of the occlusal reconstruction of the upper and lower jaws, an occlusal fine adjustment of the upper and lower jaws can be achieved, thereby adjusting the occlusal relationship between the maxillary and mandibular teeth. When it is necessary, posterior teeth of mandibular dentition are moved further, which can achieve the overall adduction of the mandibular dentition, and finally realize the orthodontic of the mandibular positioning facial retrognathism.

BRIEF DESCRIPTION OF THE DRAWINGS

The foregoing characteristics, technical features, advantages and implementations are further described below in a clear and easy-to-understand manner by describing preferred implementations with reference to the accompanying drawings.

DETAILED DESCRIPTION

To describe the technical solutions in the embodiments of the present invention or the existing technology more clearly, specific embodiments of the present invention are described below with reference to accompanying drawings. Obviously, the accompanying drawings in the following descriptions are merely some embodiments of the invention, and a person of ordinary skill in the art may further obtain other drawings according to the accompanying drawings without creative efforts, and obtain other embodiments.

Currently, for a case of facial retrognathism, an invisible appliance is used for treatment in a whole process, and needs to be completed with the help of other dental auxiliary devices, such as an anterior tractor and a traction hook. In this process, a shape of the invisible appliance changes accordingly. For the invisible appliance prepared by using a design method for the invisible appliance for facial retrognathism, if a dental auxiliary device is designed directly on the invisible appliance, a treatment effect cannot be predicted for a type and a position of the added dental auxiliary device. The dental auxiliary device is worn by a patient after being directly prepared, a orthodontic result is only determined by clinical experience of a clinician, and therefore, there is a treatment risk. Consequently, improvements are made on the invisible appliance, and the verification of different orthodontic effects is performed on the premise that an expected treatment effect is achieved, which can effectively reduce the treatment risk.

In the field of dental orthodontic, there is no comprehensive orthodontic for mandibular positioning facial retrognathism by means of the invisible appliance. Therefore, treating mandibular positioning facial retrognathism by using the invisible dental orthodontic method is of great significance.

Figure 1:
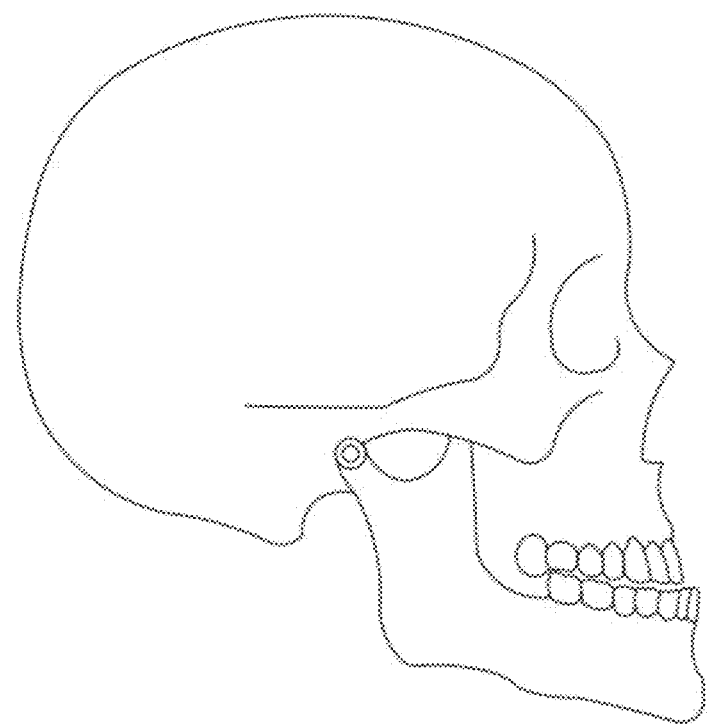
FIG. 1 is an exemplary diagram of an initial jaw in a mandibular positioning facial retrognathism orthodontic system in some embodiments of the present disclosure.

Based on this, some embodiments of the present disclosure provide a mandibular positioning facial retrognathism orthodontic system. The mandibular positioning facial retrognathism is mainly caused by inertial protrusion of the lower jaw, the upper jaw is slightly or moderately hypoplastic, and the morphology of the lower jaw is better and into a flat rectangle. A clinical orthodontic feature of the mandibular positioning facial retrognathism is that the lower jaw may be forced to be retracted until upper and lower anterior incisors are aligned, and posterior tooth opening is caused by a deep curve of Spee of the lower jaw. FIG. 1 is an exemplary diagram of an initial jaw. In some embodiments, a core point is to force a protruding lower jaw to be retracted until upper and lower anterior incisors are aligned, and based on this, a maxillary reverse traction is applied, to finally achieve an objective of remodeling and occlusal reconstruction of the jaw bones, realize simultaneous orthopaedic orthodontic, and further can effectively improve invisible treatment of the facial retrognathism.

Figure 2:
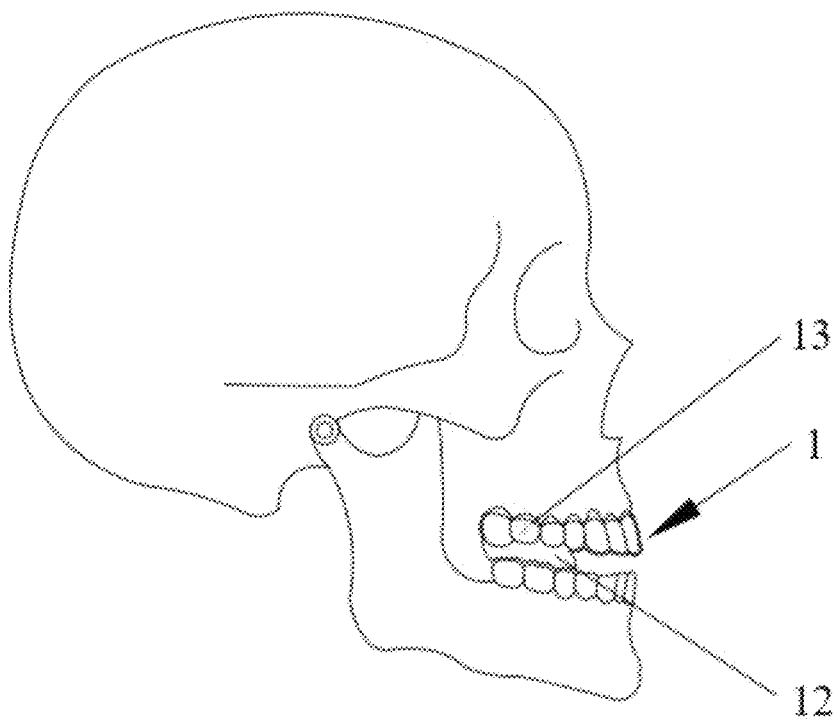
FIG. 2 is an exemplary diagram of wearing and using a mandibular positioning facial retrognathism orthodontic system provided with a protrusion portion and a retaining portion in some embodiments of the present disclosure.
Figure 3:
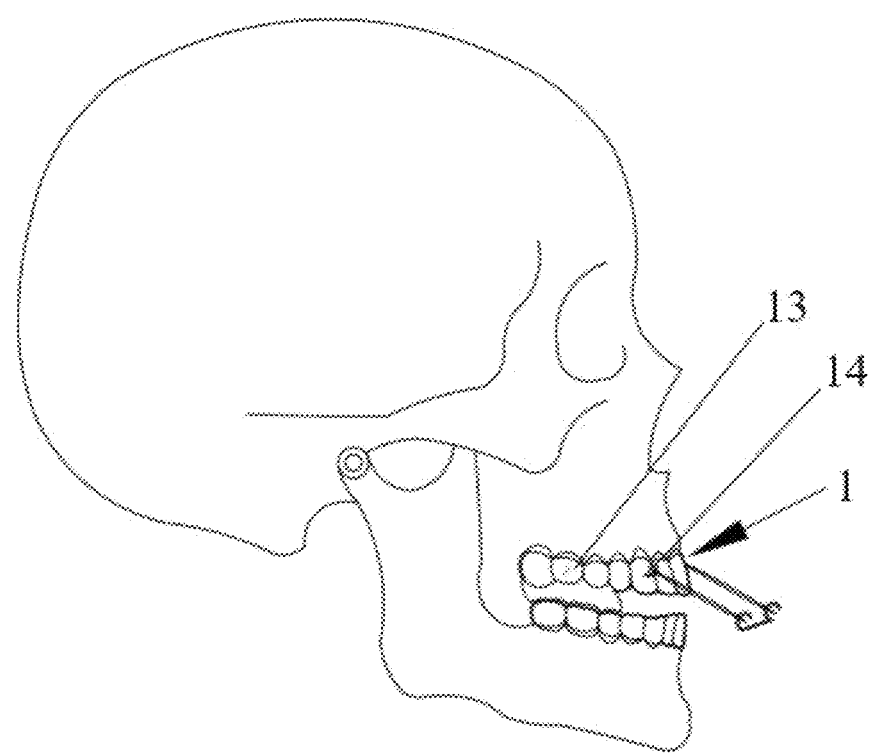
FIG. 3 is an exemplary diagram of wearing and using a mandibular positioning facial retrognathism orthodontic system provided with an anterior tractor in some embodiments of the present disclosure.
Figure 4:
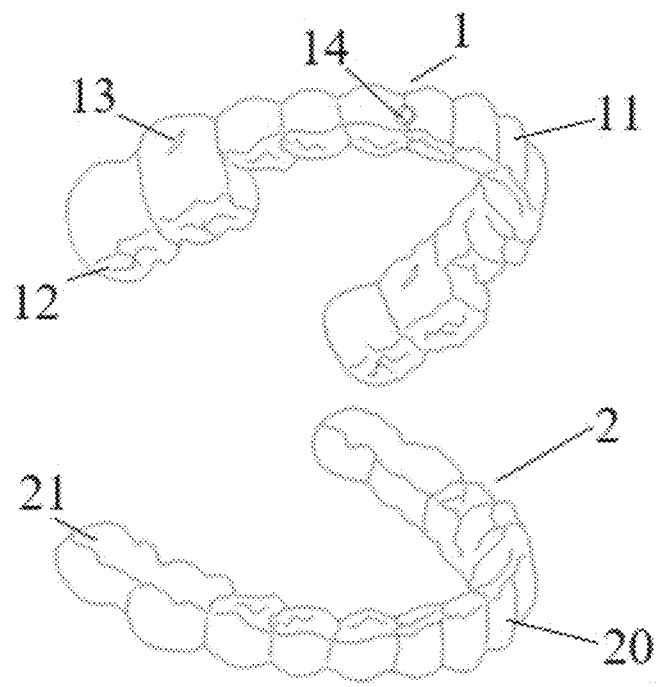
FIG. 4 is an exemplary diagram of a mandibular positioning facial retrognathism orthodontic system in some embodiments of the present disclosure.

Referring to FIG. 2 to FIG. 4, the mandibular positioning facial retrognathism orthodontic system is set for a whole efficient invisible treatment process of the facial retrognathism. In some embodiments, the system includes an anatomical/non-anatomical protrusion portion on a transparent shell-like body 11, which is engaged with a specially designed attachment. For example, referring to FIG. 2, a retaining attachment wrapped by a retaining portion 13, to make the lower jaw retracted to be aligned with the anterior incisor after the retaining attachment is worn. The protrusion portion 12 is engaged with a mandibular posterior area for occlusal reconstruction, so that mandibular incisors are aligned with maxillary incisors. Referring to FIG. 3, the traction portion 14 is engaged with a maxillary for extra-maxillary reverse traction for remodeling and occlusal reconstruction of the jaw bones; and a shape of an anterior area of a maxillary shell-like dental appliance 1 gradually changes, so that corresponding teeth are gradually aligned from an initial position to a target orthodontic position, and a height of the protrusion portion 12 disposed on the maxillary shell-like dental appliance 1 gradually decreases with the change of the shape of the anterior area of the maxillary shell-like dental appliance 1, to realize both orthopedics and tooth orthodontic.

Referring to FIG. 2 to FIG. 5 still, the mandibular positioning facial retrognathism orthodontic system includes the maxillary shell-like dental appliance 1 with a shell-like body 11, here the shell-like body 11 is provided with a plurality of cavities for accommodating teeth, a protrusion portion 12 protruding toward an opposite jaw is disposed at a posterior area corresponding to the shell-like body 11, a traction portion 14 is disposed on a labial side of the shell-like body 11, and a retaining portion 13 configured for fastening with a retaining attachment is disposed at the posterior area corresponding to the shell-like body 11.

As shown in FIG. 4, the protrusion portion 12 plays a role of enabling that the mandibular incisors tend to be aligned with the maxillary incisors during occlusal reconstruction of the upper and lower jaws, and an occlusal relative position of the upper and lower jaws is more stable. A design of the protrusion portion 12 not only has an effect of opening patient's occlusion on the lower jaw of the patient, but also has an occlusal induction effect, to avoid a orthodontic limitation of the anterior area. More specifically, a setting height of the protrusion portion 12 relative to a vertical direction of the occlusal surface may enable the lower jaw to be retracted until the mandibular incisors tend to be aligned with the maxillary incisors when the maxillary shell-like dental appliance 1 is engaged with the mandibular posterior area for occlusion, thereby achieving the effect of inducing the lower jaw to be retracted. Because the maxillary shell-like dental appliance 1 is made of a transparent material, an outer surface of the maxillary shell-like dental appliance 1 (that is, a back surface in contact with the teeth) has a specific degree of smoothness. To keep stable during occlusion between the maxillary shell-like dental appliance 1 and the mandibular teeth, in some embodiments, a part of the protrusion portion 12 facing an opposing jaw dentition occlusal surface is further provided with a friction portion.

Specifically, the friction portion is of one, two or a combination of more than two of a structure with a matte surface, a structure with bumps, a structure with a hollowed surface, or a structure with a porous surface. For example, the friction portion may be of a structure whose surface has a combination of matte and bumps, or the friction portion may be a structure whose surface is a combination of matte, bumps, and holes. In some embodiments of the present disclosure, a shape of the surface of the friction portion is not specifically limited, and a person skilled in the art may design, according to a stable function achieved by the friction portion, structures of other shapes with the stable function.

In addition, in some embodiments, as shown in FIG. 4, the maxillary shell-like dental appliance 1 further includes a retaining portion 13, so that the maxillary shell-like dental appliance 1 is configured for fastening with the retaining attachment through the retaining portion 13, to prevent the maxillary shell-like dental appliance 1 from being fallen off from teeth engaged with the maxillary shell-like dental appliance. In addition, in some embodiments, a retaining portion 13 is disposed on a labial and/or buccal side of an outer surface of the maxillary shell-like dental appliance 1, and the retaining portion 13 is provided with at least one retaining attachment designed on the teeth to complete the retention. Specifically, the retaining portion 13 has at least two surfaces, and each of the outer surfaces of the retaining portion 13 is disposed at a specific angle relative to the labial side of the maxillary shell-like dental appliance 1. Specifically, the retaining portion 13 may include a first curved surface and a second curved surface, the first curved surface and the second curved surface jointly define an accommodating space of the retaining attachment that having an open end and a closed end, bending directions of the first curved surface and the second curved surface are the same, and curvatures of the first curved surface and the second curved surface are different. The retaining attachment may be disposed in the accommodating space of the retaining attachment, to achieve a retention force between the maxillary shell-like dental appliance 1 and the teeth, and the curvatures of the first curved surface and the second curved surface are different, to increase the retention force. Especially, an included angle formed between a tangential direction at any point on the first curved surface and a tangential direction at any point on the second curved surface is an acute angle, to increase a contact area and a retention force of the maxillary shell-like dental appliance and the teeth. Before the maxillary shell-like dental appliance 1 is in contact with the teeth, the retaining portion 13 is engaged with and is fasten to the retaining attachment on corresponding teeth, and one of surfaces of the retaining portion 13 is a surface that increases the retention force between the maxillary shell-like dental appliance 1 and the teeth.

In addition, in some embodiments, according to a traction direction of the maxillary shell-like dental appliance 1 to the teeth, when the retaining portion 13 is designed, a force application surface of the retaining portion 13 to the retaining attachment of the teeth is perpendicular to the traction direction, thereby increasing the retention force between the maxillary shell-like dental appliance 1 and the teeth.

In addition, according to a shape of matching between the maxillary shell-like dental appliance 1 and the teeth, depths of the maxillary shell-like dental appliance 1 warping the teeth at different positions are different. To optimize a design position of the retaining portion 13, in some embodiments, the retaining attachment is disposed on a buccal surface of the posterior area and/or the lip-side surface of the teeth. Therefore, the retaining portion 13 is also correspondingly disposed on a buccal surface of the posterior area of the maxillary shell-like dental appliance 1 and/or the lip-side surface.

A traction portion 14 is designed on a side of a surface of the maxillary shell-like dental appliance 1 facing away from interior of the cavity. In some embodiments, through the design of the traction portion 14, the designed maxillary shell-like dental appliance 1 can achieve extramaxillary traction through the traction portion 14, as shown in FIG. 4. The traction portion 14 may be subsequently added to the shell-like body 11. Specifically, the shell-like body 11 is provided with a structure that is engaged with and is equipped with the traction portion 14. The structure for engagement and equipment may be a hole that matches the traction portion 14 and is provided on the maxillary shell-like dental appliance 1; or an inner surface and the outer surface of the maxillary shell-like dental appliance 1 are engaged with and are equipped with the traction portion 14 by engagement; or the structure for engaging with the maxillary shell-like dental appliance 1 and the traction portion 14 is a bonding structure. Alternatively, according to the structure complexity of the traction portion 14, a corresponding design manner may be selected. For example, production is performed by film pression, or production is performed by 3D direct printing.

The retaining portion 13 and the traction portion 14 are disposed on the maxillary shell-like dental appliance 1. When the two are engaged for extramaxillary traction, the traction portion 14 is in traction connection with the anterior tractor or the intermaxillary traction member, the traction portion pulls the shell-like body 11 to cause the teeth to move, the traction portion 14 serves as a force application party, the retaining portion 13 interacts with the retaining attachment as a whole, and acts as a force receiving party of the traction portion 14, and a force receiving direction is perpendicular to a force application direction in which the traction portion 14 is generated, to prevent the shell-like body 11 from being deformed and being fallen from the teeth during traction.

In summary, interaction of the protrusion portion 12, the traction portion 14, and the retaining portion 13 enables the mandibular positioning facial retrognathism orthodontic system to complete the remodeling and occlusal reconstruction of the jaw bones. Specifically, the protrusion portion 12 is engaged with the mandibular posterior area for occlusal reconstruction, so that mandibular incisors are aligned with maxillary incisors; the traction portion 14 is engaged with a maxillary for extramaxillary reverse traction for orthodontic and remolding of jaw bones; and the retaining portion 13 is configured for fastening with the retaining attachment, to prevent the maxillary shell-like dental appliance 1 from being fallen off from teeth engaged with the maxillary shell-like dental appliance.

Figure 5:
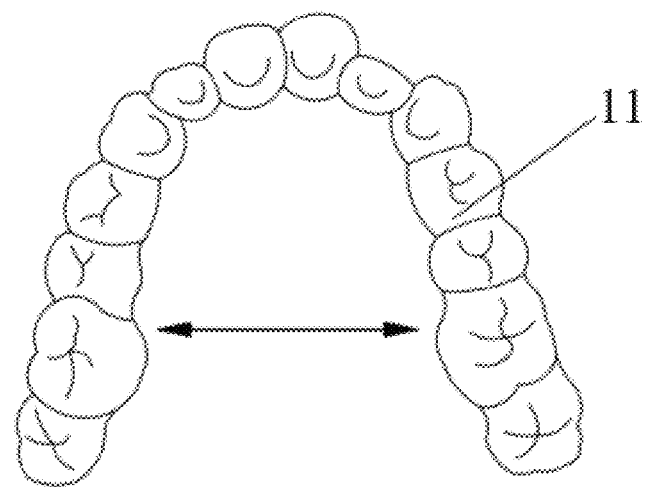
FIG. 5 is an exemplary diagram of a mandibular positioning facial retrognathism orthodontic system for bow expansion in some embodiments of the present disclosure.

In some embodiments, as shown in FIG. 5, the mandibular positioning facial retrognathism orthodontic system may further include horizontal arch expansion for improving the occlusal relationship.

As the orthodontic process proceeds, during the orthodontic and remolding of the jaw bones, a height of the protrusion portion 12 disposed on a different maxillary shell-like dental appliance 1 gradually decreases with a change of a shape of an anterior area of the maxillary shell-like dental appliance 1, and the shape of the anterior area of the maxillary shell-like dental appliance 1 gradually changes, so that corresponding teeth are gradually aligned from an initial position to a target orthodontic position, to implement both jaw bone orthopedics and tooth orthodontic.

In addition, some embodiments of the present disclosure further provide a mandibular positioning facial retrognathism orthodontic system, and as shown in FIG. 4, the mandibular positioning facial retrognathism orthodontic system provided in some embodiments further includes a mandibular shell-like dental appliance 2, here the mandibular shell-like dental appliance 2 includes a shell-like body 20 with a plurality of cavities for accommodating mandibular teeth, and a shape of an anterior area of the mandibular shell-like dental appliance 2 gradually changes during orthodontic remolding of the jaw bones, so that corresponding teeth are gradually depressed from an initial position to a target orthodontic position. In addition, in some embodiments, as shown in FIG. 4, the shell-like dental appliance is worn in both the upper and lower jaws. The maxillary shell-like dental appliance 1 is worn in the upper jaw, and the mandibular shell-like dental appliance 2 is worn in the lower jaw, to implement simultaneous orthodontic of the upper and lower jaws. Specifically, when the upper jaw simultaneously undergoes the jaw bone orthopedics and the dental orthodontic, and the mandibular shell-like dental appliance 2 also performs orthodontic on the mandibular teeth.

The mandibular shell-like dental appliance 2 further includes a limiting portion. As shown in FIG. 4, the limiting portion is an opening 21 or a protrusion toward an opposite jaw. The opening 21 is an opening 21 designed in a position of the protrusion portion 12 designed in the mandibular shell-like dental appliance 2 corresponding to the maxillary shell-like dental appliance 1. When the maxillary shell-like dental appliance 1 is engaged with the mandibular shell-like dental appliance 2, the protrusion portion 12 of the maxillary shell-like dental appliance 1 is limited to be located in the opening 21 of the mandibular shell-like dental appliance. Similarly, the protrusion is a protrusion designed in a position of the protrusion portion 12 designed in the mandibular shell-like dental appliance 2 corresponding to the maxillary shell-like dental appliance 1. When the maxillary shell-like dental appliance 1 is engaged with the mandibular shell-like dental appliance 2, the protrusion portion 12 of the maxillary shell-like dental appliance 1 is limited to be located in the protrusion of the mandibular shell-like dental appliance 2. When a protrusion is also designed in the position of the protrusion portion 12 designed in the mandibular shell-like dental appliance 2 corresponding to the maxillary shell-like dental appliance 1, to increase the friction between the two, in some embodiments, a part of the protrusion portion protruding toward the maxillary shell-like dental appliance 1 is provided with a reinforcing portion that increases the friction with the maxillary shell-like dental appliance 1. Specifically, the reinforcing portion is of one, two, or a combination of more than two of a structure with a matte surface, a structure with bumps, or a structure with a hollowed surface. For example, the reinforcing portion may be of a combined structure with matte and bumps.

When the maxillary shell-like dental appliance 1 is worn on the maxillary teeth of the patient, and the mandibular shell-like dental appliance 2 is worn on the mandibular teeth of the patient, and before the maxillary shell-like dental appliance 1 is engaged with the mandibular shell-like dental appliance 2, the protrusion portion 12 is limited in the opening 21, the mandibular incisors tend to be aligned with the maxillary incisors during occlusal reconstruction of the upper and lower jaws, and an occlusal relative position of the upper and lower jaws is more stable. A design of the protrusion portion 12 not only has an effect of opening the patient's occlusion on the lower jaw of the patient, but also has an occlusal induction effect, to avoid a orthodontic limitation of the anterior area. In addition, the traction portion 14 is engaged with the external anterior tractor to increase the traction force, to complete the reverse traction of the upper jaw. Through the design of the retaining portion 13, a contact area and a retention force between the maxillary shell-like dental appliance 1 and the teeth can be increased, and the retaining portion 13 may further be engaged with the traction portion 14. During traction, the traction portion 14 is in traction connection with the anterior tractor or the intermaxillary traction member, the traction portion 14 pulls the shell-like body 11 to cause the teeth to move, the traction portion 14 serves as a force application party, the retaining portion 13 interacts with the retaining attachment as a whole, and acts as a force receiving party of the traction portion, and a force receiving direction is perpendicular to a force application direction in which the traction portion 14 is generated, to prevent the shell-like body 11 from being deformed and being fallen from the teeth during traction.

In addition, in some embodiments, the mandibular positioning facial retrognathism orthodontic system may further include horizontal arch expansion for improving the occlusal relationship, as shown in FIG. 5.

It should be noted that, a shape of an anterior area of the mandibular shell-like dental appliance 2 gradually changes during orthodontic remolding of the jaw bones, so that corresponding teeth are gradually depressed from an initial position to a target orthodontic position. As the shape of the anterior area of the mandibular shell-like dental appliance 2 gradually depresses, correspondingly, a height of the protrusion portion 12 disposed on a different maxillary shell-like dental appliance 1 may be designed to gradually decrease, and this is only a partial example of a better implementation solution.

Figure 6:
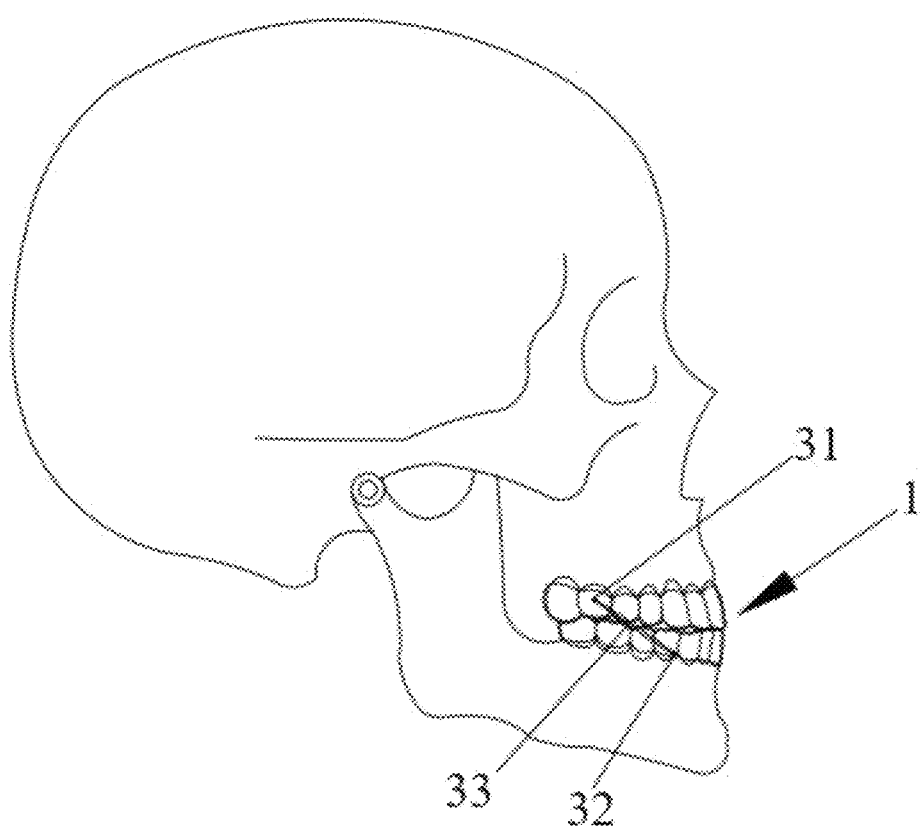
FIG. 6 is an exemplary diagram of a mandibular positioning facial retrognathism orthodontic system in some embodiments of the present disclosure.

In addition, some embodiments of the present disclosure further provide a mandibular positioning facial retrognathism orthodontic system. For example, referring to FIG. 6, the mandibular positioning facial retrognathism orthodontic system provided in some embodiments further includes a first intermaxillary traction member 31 disposed on the maxillary shell-like dental appliance 1 and a second intermaxillary traction member 32 disposed on the mandibular shell-like dental appliance 2, and after orthodontic remolding of the jaw bones, the first intermaxillary traction member 31 and the second intermaxillary traction member 33 are connected by an elastic member, so that an occlusal relationship between maxillary and mandibular teeth is adjusted. Specifically, through orthodontic remolding of the bones of the maxillary shell-like dental appliance 1, and using an occlusal fine adjustment as a main objective, class III intermaxillary traction may be performed by using the first intermaxillary traction member 31 and the second intermaxillary traction member 32, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class III intermaxillary traction. The posterior teeth of the mandibular dentition may further be moved further according to orthodontic requirements, to better implement the overall adduction of the mandibular dentition and implement the maxillary and mandibular occlusal fine adjustment.

The first intermaxillary traction member 31 is engaged with the second intermaxillary traction member 32 by using the elastic member 33 to implement traction, here the elastic member 33 may be an elastic rope or a spring used in a mouth. For a structure design of the first intermaxillary traction member 31 and the second intermaxillary traction member 32, reference can be made to the form of the foregoing traction portion 14, and the first intermaxillary traction member and the second intermaxillary traction member may alternatively be other auxiliary devices with a hooking function. Details are not described herein.

Therefore, it is not difficult to see that the mandibular positioning facial retrognathism orthodontic system provided in some embodiments includes following components.

A maxillary shell-like dental appliance 1 having a shell-like body 11, here a plurality of cavities for accommodating teeth are provided on the shell-like body 11, a protrusion portion 12 protruding toward an opposite jaw is disposed at a posterior area corresponding to the shell-like body 11, a traction portion 14 is disposed on a labial side of the shell-like body 11, and a retaining portion 13 configured for fastening with a retaining attachment is disposed at the posterior area corresponding to the shell-like body 11; the protrusion portion 12 is engaged with the mandibular posterior area for occlusal reconstruction, so that mandibular incisors are aligned with maxillary incisors; the traction portion 14 is engaged with a maxillary for extramaxillary reverse traction for orthodontic remolding of jaw bones; and a shape of an anterior area of the maxillary shell-like dental appliance 1 gradually changes, so that corresponding teeth are gradually aligned from an initial position to a target orthodontic position, and a height of the protrusion portion 12 disposed on the maxillary shell-like dental appliance 1 gradually decreases with the change of the shape of the anterior area of the maxillary shell-like dental appliance 1.

A mandibular shell-like dental appliance 2, here the mandibular shell-like dental appliance 2 includes a shell-like body 20 provided with a plurality of cavities for accommodating mandibular teeth, and a shape of an anterior area of the mandibular shell-like dental appliance 2 gradually changes during orthodontic remolding of the jaw bones, so that corresponding teeth are gradually depressed from an initial position to a target orthodontic position.

After orthodontic remolding of the jaw bones is completed for the upper and lower jaws, and an occlusal fine adjustment is used as a main objective, class III intermaxillary traction may be performed by using the first intermaxillary traction member 31 and the second intermaxillary traction member 32, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class III intermaxillary traction. Specifically, a first intermaxillary traction member 31 is disposed on the maxillary shell-like dental appliance 1 and a second intermaxillary traction member 32 is disposed on the mandibular shell-like dental appliance 2, and after orthodontic remolding of the jaw bones, the first intermaxillary traction member 31 and the second intermaxillary traction member 32 are connected by an elastic member 33, so that an occlusal relationship between maxillary and mandibular teeth is adjusted.

Figure 7:
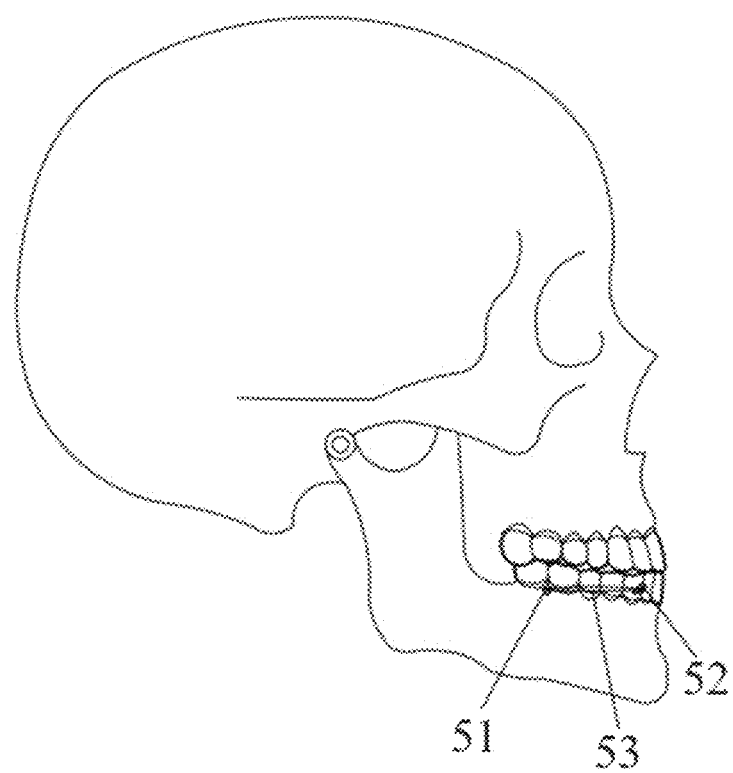
FIG. 7 is an exemplary diagram of another mandibular positioning facial retrognathism orthodontic system in some embodiments of the present disclosure.

In addition, some embodiments of the present disclosure further provide a mandibular positioning facial retrognathism orthodontic system, and referring to FIG. 7, the mandibular positioning facial retrognathism orthodontic system provided in some embodiments further includes an intramaxillary traction member 52 disposed on the mandibular shell-like dental appliance 2 and an implant anchorage member 51 disposed on a mandibular alveolar bone, and after orthodontic remolding of the jaw bones, the implant anchorage member 51 and the intramaxillary traction member 52 are connected by an elastic member 53, so that the occlusal relationship between the maxillary and mandibular teeth is adjusted. Specifically, through orthodontic remolding of the bones of the maxillary shell-like dental appliance 1, and using an occlusal fine adjustment as a main objective, class I intramaxillary traction may be performed by using the intramaxillary traction member 52. That is, the implant anchorage member 51, for example, an implant anchorage nail, is planted on the upper jaw or the lower jaw. The implant anchorage member and a maxillary traction member are hooked in the same jaw or the implant anchorage member and a hookable member, such as a traction hook, disposed on the jaw shell-like dental appliance are connected through an elastic member, such as a rubber for intraoral orthodontic, to implement the class I intramaxillary traction. The posterior teeth of the mandibular dentition may further be moved further according to orthodontic requirements, to better implement the overall adduction of the mandibular dentition and implement the maxillary and mandibular occlusal fine adjustment.

During orthodontic treatment, any force applied to the teeth to cause the teeth to move must simultaneously produce a force with an opposite direction and a same magnitude, and a case of supporting a reaction force caused by moving the corrected teeth is referred to as "anchorage". Actually, the anchorage is a basis for providing and generating a tooth orthodontic force. Generally, in orthodontic treatment, the anchorage portion mainly includes non-orthodontic teeth, and a palate and an alveolar may also be used as the anchorage portion. The function of an anchorage force is an opposite direction force generated when an orthodontic force is applied to the teeth of the anchorage portion. Anchorages are divided into an intramaxillary anchorage, an intermaxillary anchorage, and an extramaxillary anchorage. In some embodiments, the intramaxillary anchorage is used, and the implant anchorage member is implemented in many structure solutions. A main function of some embodiments of the present disclosure is to implement the overall adduction of the mandibular dentition, and therefore implement the maxillary and mandibular occlusal fine adjustment.

Therefore, it is not difficult to see that the mandibular positioning facial retrognathism orthodontic system provided in the foregoing some embodiments includes following components.

A maxillary shell-like dental appliance 1 having a shell-like body 11, here a plurality of cavities for accommodating teeth are provided on the shell-like body 11, a protrusion portion 12 protruding toward an opposite jaw is disposed at a posterior area corresponding to the shell-like body 11, a traction portion 14 is disposed on a labial side of the shell-like body 11, and a retaining portion 13 configured for fastening with a retaining attachment is disposed at the posterior area corresponding to the shell-like body 11; the protrusion portion 12 is engaged with the mandibular posterior area for occlusal reconstruction, so that mandibular incisors are aligned with maxillary incisors; the traction portion 14 is engaged with a maxillary for extramaxillary reverse traction for orthodontic remolding of jaw bones; and a shape of an anterior area of the maxillary shell-like dental appliance 1 gradually changes, so that corresponding teeth are gradually aligned from an initial position to a target orthodontic position, and a height of the protrusion portion 12 disposed on the different maxillary shell-like dental appliance 1 in the orthodontic system gradually decreases with the change of the shape of the anterior area of the maxillary shell-like dental appliance 1.

A mandibular shell-like dental appliance 2, here the mandibular shell-like dental appliance 2 includes a shell-like body 20 provided with a plurality of cavities for accommodating mandibular teeth, and a shape of an anterior area of the mandibular shell-like dental appliance 2 gradually changes during orthodontic remolding of the jaw bones, so that corresponding teeth are gradually depressed from an initial position to a target orthodontic position.

After orthodontic remolding of the bones is completed for the upper and lower jaws, and an occlusal fine adjustment is used as a main objective, class I intramaxillary traction may be performed by using the intramaxillary traction member 52, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class I intramaxillary traction. Specifically, an intramaxillary traction member 52 disposed on the mandibular shell-like dental appliance 2 and an implant anchorage member 51 disposed on a mandibular dento-alveolar bone, and after orthodontic remolding of the jaw bones, the implant anchorage member 51 and the intramaxillary traction member 52 are connected by an elastic member 53, so that the occlusal relationship between the maxillary and mandibular teeth is adjusted.

Figure 8:
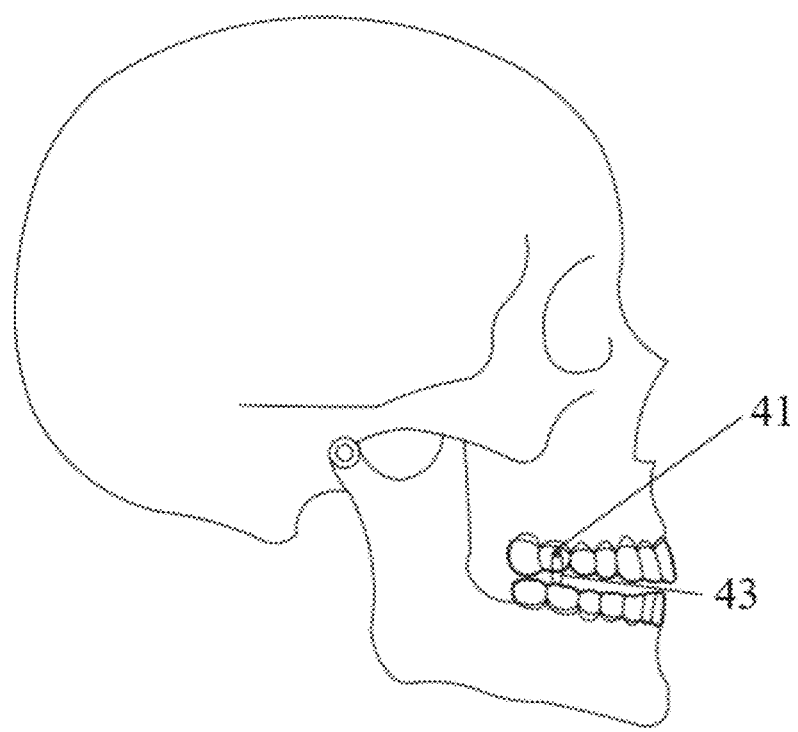
FIG. 8 is an exemplary diagram of another mandibular positioning facial retrognathism orthodontic system in some embodiments of the present disclosure.
Figure 9:
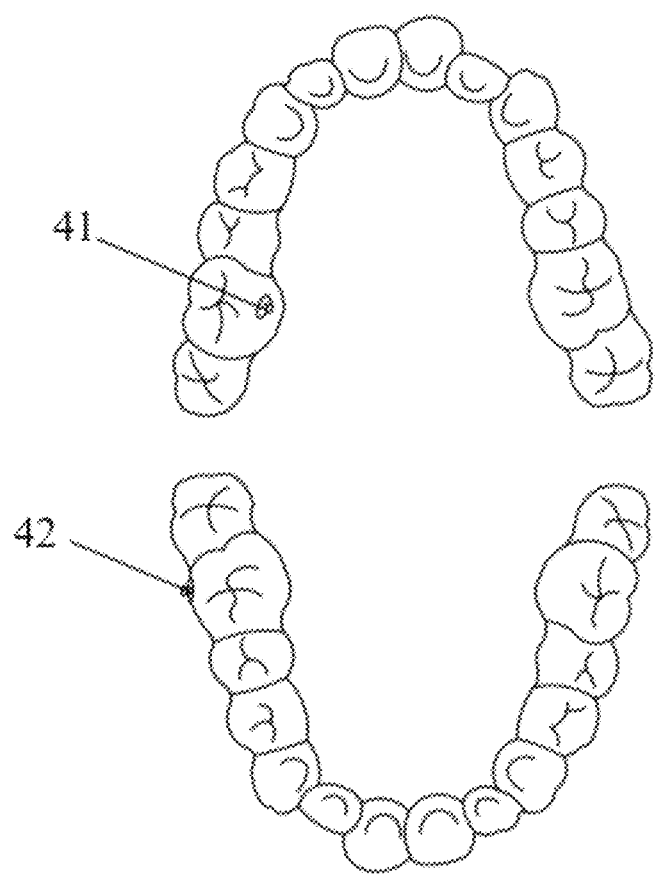
FIG. 9 is an exemplary diagram of a mandibular positioning facial retrognathism orthodontic system including a maxillary shell-like dental appliance from a bottom view and a maxillary shell-like dental appliance from a top view in some embodiments of the present disclosure.
Figure 10:
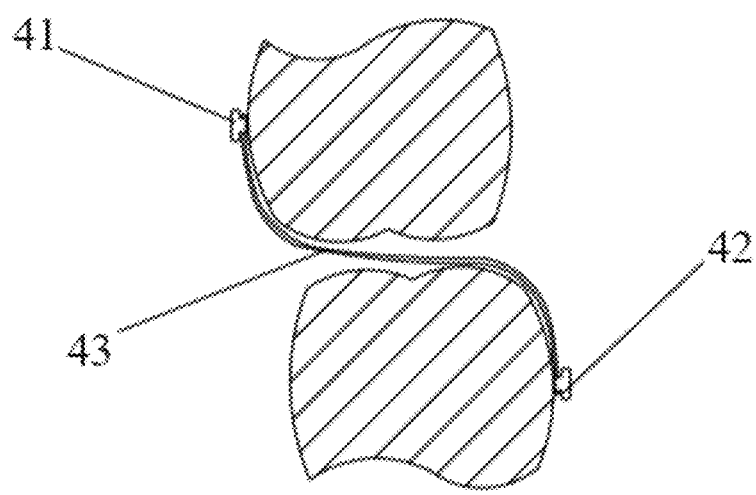
FIG. 10 is a partial cross-sectional exemplary diagram of a mandibular positioning facial retrognathism orthodontic system in some embodiments of the present disclosure.

In addition, referring to FIG. 8 to FIG. 10, some embodiments of the present disclosure further provide a mandibular positioning facial retrognathism orthodontic system. The mandibular positioning facial retrognathism orthodontic system further includes a first interactive traction member 41 disposed on the maxillary shell-like dental appliance 1 and a second interactive traction member 42 disposed on the mandibular shell-like dental appliance 2, and after orthodontic remolding of the jaw bones and before adjusting the occlusal relationship between the maxillary and mandibular teeth, the first interactive traction member 41 and the second interactive traction member 42 are connected by an elastic member 43, so that posterior teeth are released from jaw opening. Specifically, a main objective is to release the posterior teeth from jaw opening. If the jaw opening is relatively large, the upper and lower interactive traction is engaged to reduce a jaw opening degree of the upper and lower jaws. The first interactive traction member 41 and the second interactive traction member 42 of the upper and lower jaws may be traction members that may generate hooking forces, which are respectively disposed on a buccal side and a labial side of the upper and lower jaws, or are disposed on a labial side or a buccal side of the upper and lower jaws. That is, the first interactive traction member 41 and the second interactive traction member 42 are respectively disposed on different sides of the buccal side and the labial side of the upper and lower jaws. Specifically, the first interactive traction member 41 is disposed on the buccal side of the upper jaw, and the second interactive traction member 42 is disposed on the labial side of the lower jaw; or the second interactive traction member 42 is disposed on the labial side of the upper jaw, and the first interactive traction member 41 is disposed on the buccal side of the lower jaw. As shown in FIG. 8 and FIG. 10, the first interactive traction member 41 and the second interactive traction member 42 may be connected by an elastic member 43, to implement the interactive traction of the upper and lower jaws and reduce the degree of jaw opening.

It may be learned from FIG. 8 and FIG. 9 that the first interactive traction member 41 and the second interactive traction member 42 may be a traction member disposed in a tooth area, or may be a plurality of traction members disposed in a plurality of tooth areas. In some embodiments, for the first interactive traction member 41 and the second interactive traction member 42, specific positions of the tooth area in which the first interactive traction member 41 and the second interactive traction member 42 are disposed and set quantities may be arranged according to a jaw opening situation. Therefore, "a" such as "a first interactive traction member 41/a second interactive traction member 42" mentioned later is merely an imaginary number, and does not limit a quantity of traction members. Similarly, positions of the tooth area in which the first interactive traction member 41 and the second interactive traction member 42 are disposed in the accompanying drawings are merely examples and are not limited thereto.

Therefore, it is not difficult to see that the mandibular positioning facial retrognathism orthodontic system provided in the foregoing some embodiments includes following components.

A maxillary shell-like dental appliance 1 having a shell-like body 11, here a plurality of cavities for accommodating teeth are provided on the shell-like body 11, a protrusion portion 12 protruding toward an opposite jaw is disposed at a posterior area corresponding to the shell-like body 11, a traction portion 14 is disposed at a labial side of an outer surface of the shell-like body 11 in contact with the teeth, and a retaining portion 13 configured for fastening with a retaining attachment is disposed at the posterior area corresponding to the shell-like body 11; the protrusion portion 12 is engaged with the mandibular posterior area for occlusal reconstruction, so that mandibular incisors are aligned with maxillary incisors; the traction portion 14 is engaged with a maxillary for extramaxillary reverse traction for orthodontic remolding of jaw bones; and a shape of an anterior area of the maxillary shell-like dental appliance 1 gradually changes, so that corresponding teeth are gradually aligned from an initial position to a target orthodontic position, and a height of the protrusion portion 12 disposed on the maxillary shell-like dental appliance 1 gradually decreases with the change of the shape of the anterior area of the maxillary shell-like dental appliance 1.

A mandibular shell-like dental appliance 2, here the mandibular shell-like dental appliance 2 includes a shell-like body 20 provided with a plurality of cavities for accommodating mandibular teeth, and a shape of an anterior area of the mandibular shell-like dental appliance 2 gradually changes during orthodontic remolding of the jaw bones, so that corresponding teeth are gradually depressed from an initial position to a target orthodontic position.

After orthodontic remolding of the jaw bones and before adjusting of the occlusal relationship between the maxillary and mandibular teeth, a first interactive traction member 41 is disposed on the maxillary shell-like dental appliance 1, a second interactive traction member 42 is disposed on the mandibular shell-like dental appliance 2, the first interactive traction member 41 and the second interactive traction member 42 are connected by an elastic member 43, so that posterior teeth are released from jaw opening.

After that, using an occlusal fine adjustment as a main objective, class III intermaxillary traction may be performed by using the intermaxillary traction member, and an attachment of the maxillary and mandibular dentition may be replaced according to orthodontic requirements. That is, the retaining attachment is removed from the teeth, and is replaced with an attachment suitable for the occlusal fine adjustment. For example, a traction member for class III intermaxillary traction. Specifically, a first interactive traction member 41 disposed on the maxillary shell-like dental appliance 1 and a second interactive traction member 42 disposed on the mandibular shell-like dental appliance 2, and after orthodontic remolding of the jaw bones, the first interactive traction member 41 and the second interactive traction member 42 are connected by an elastic member 43, so that an occlusal relationship between maxillary and mandibular teeth is adjusted.

Figure 11:
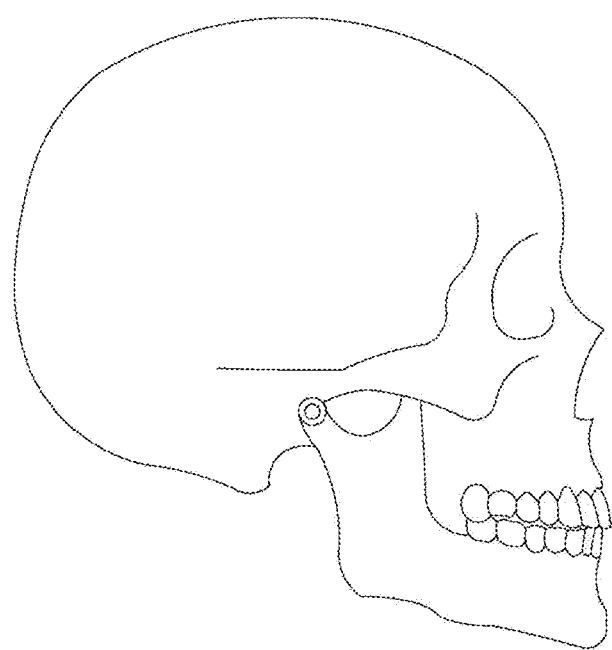
FIG. 11 is an exemplary diagram of a dental jaw after orthodontic in a mandibular positioning facial retrognathism orthodontic system in some embodiments of the present disclosure.

After orthopedic reconstruction of the jaw bones, that is, after an improvement of the occlusal reconstruction of the upper and lower jaws, an occlusal fine adjustment of the upper and lower jaws may be implemented, to adjust the occlusal relationship between the maxillary and mandibular teeth. When it is necessary, posterior teeth of mandibular dentition are moved further, to implement the overall adduction of the mandibular dentition, and finally implement the orthodontic of the mandibular positioning facial retrognathism. FIG. 11 is an exemplary diagram of finally implementing orthodontic of mandibular positioning facial retrognathism.

Figure 12:
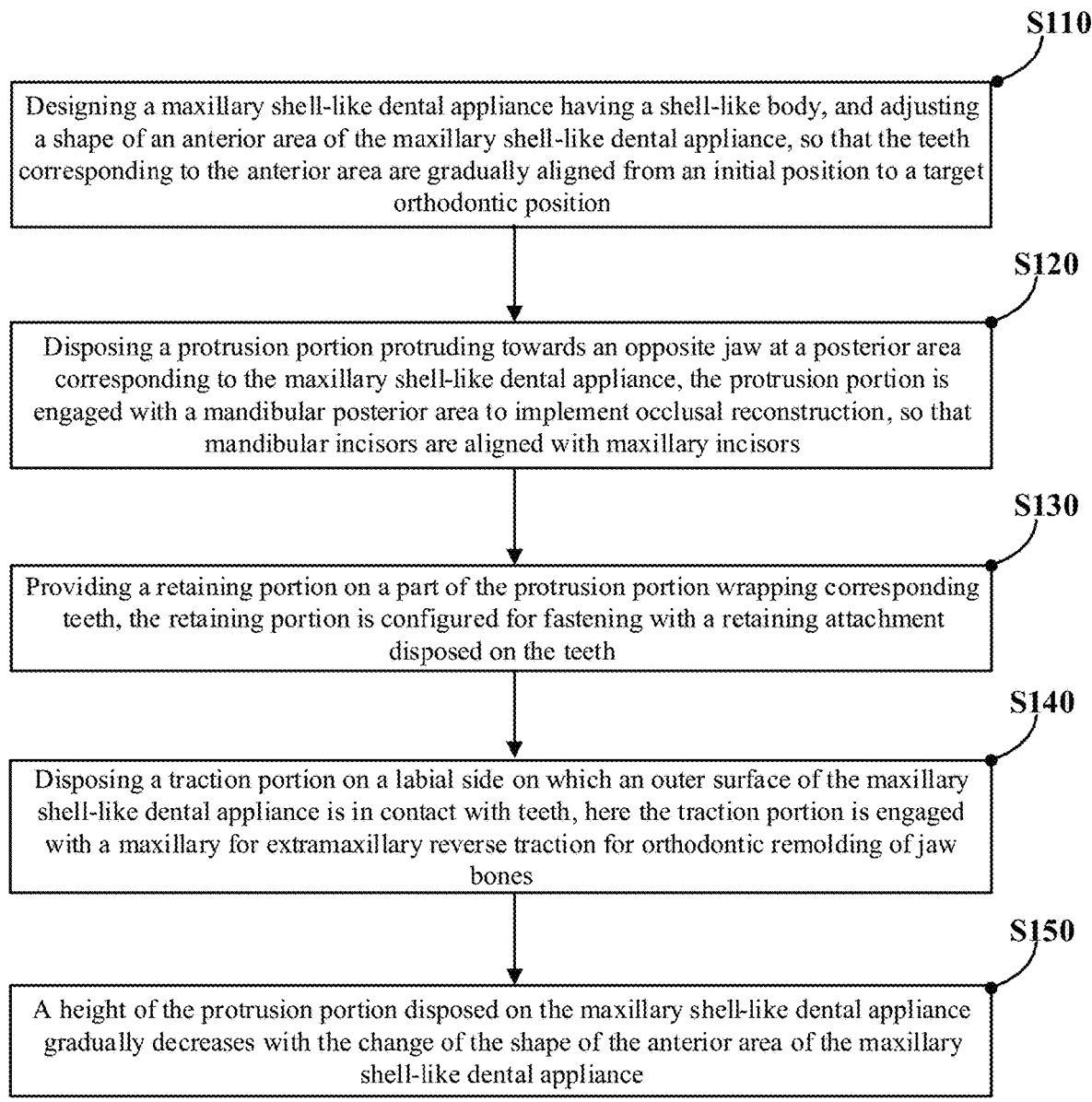
FIG. 12 is a flowchart of a design method for a mandibular positioning facial retrognathism orthodontic system in some embodiments of the present disclosure.

In addition, some embodiments of the present disclosure further provide a design method for a mandibular positioning facial retrognathism orthodontic system. FIG. 12 is a flowchart of a design method for the mandibular positioning facial retrognathism orthodontic system provided in the foregoing some embodiments. With reference to FIG. 1 to FIG. 5, the design method includes the following steps.

S110: Designing a maxillary shell-like dental appliance 1 having a shell-like body 11, and adjusting a shape of an anterior area of the maxillary shell-like dental appliance 1, so that the teeth corresponding to the anterior area are gradually aligned from an initial position to a target orthodontic position.

S120: Disposing a protrusion portion 12 protruding towards an opposite jaw at a posterior area corresponding to the maxillary shell-like dental appliance 1, here the protrusion portion 12 is engaged with a mandibular posterior area to implement occlusal reconstruction, so that mandibular incisors are aligned with maxillary incisors.

S130: Providing a retaining portion 13 on a part of the protrusion portion 12 wrapping corresponding teeth, here the retaining portion 13 is configured for fastening with a retaining attachment disposed on the teeth.

S140: Disposing a traction portion 14 on a labial side on which an outer surface of the maxillary shell-like dental appliance 1 is in contact with teeth, here the traction portion 14 is engaged with a maxillary for extramaxillary reverse traction for orthodontic remolding of jaw bones.

S150: A height of the protrusion portion 12 disposed on the maxillary shell-like dental appliance 1 gradually decreases with the change of the shape of the anterior area of the maxillary shell-like dental appliance 1.

A setting height of the protrusion portion 12 disposed on the maxillary shell-like dental appliance 1 relative to the occlusal surface in a vertical direction may enable that when the maxillary shell-like dental appliance 1 is engaged with the mandibular shell-like dental appliance 2, the mandibular incisors tend to be aligned with the maxillary incisors during occlusal reconstruction of the upper and lower jaws, and an occlusal relative position of the upper and lower jaws is more stable. A design of the protrusion portion 12 not only has an effect of opening patient's occlusion on the lower jaw of the patient, but also has an occlusal induction effect, to avoid an orthodontic limitation of the anterior area. In addition, through the design of the retaining portion 13, a contact area and a retention force between the maxillary shell-like dental appliance 1 and the teeth can be increased, and the retaining portion 13 may further be engaged with the traction portion 14. During traction, the traction portion 14 pulls the shell-like body 11 to cause the teeth to move, the traction portion 14 serves as a force application party, the retaining portion 13 interacts with the retaining attachment as a whole, and acts as a force receiving party of the traction portion 14, and a force receiving direction is perpendicular to a force application direction in which the traction portion 14 is generated, to prevent the shell-like body 14 from being deformed and being fallen from the teeth during traction.

In the mandibular positioning facial retrognathism orthodontic system designed by using the provided design method, a protruding lower jaw is forced to be retracted until upper and lower anterior incisors are aligned, and based on this, a maxillary reverse traction is applied, to finally achieve an objective of remodeling and occlusal reconstruction of the jaw bones, implement simultaneous orthopaedic orthodontic, and further implement efficient invisible treatment of facial retrognathism. The mandibular positioning facial retrognathism orthodontic system is set for a whole efficient invisible treatment process of facial retrognathism. In this embodiment, the system includes an anatomical/non-anatomical jaw pad on a transparent shell-like body 11, which is engaged with a specially designed attachment (for example, a retaining portion 13), to enable the lower jaw be retracted to the anterior incisor after the attachment is worn. The protrusion portion 12 is engaged with the mandibular posterior area for occlusal reconstruction, so that mandibular incisors are aligned with maxillary incisors; the traction portion 14 is engaged with a maxillary for extramaxillary reverse traction for remodeling and occlusal reconstruction of the jaw bones; and a shape of an anterior area of a maxillary shell-like dental appliance 1 gradually changes, so that corresponding teeth are gradually aligned from an initial position to a target orthodontic position, and a height of the protrusion portion 12 disposed on the maxillary shell-like dental appliance 1 gradually decreases with the change of the shape of the anterior area of the maxillary shell-like dental appliance 1, to implement both orthopedics and tooth orthodontic.

Figure 13:
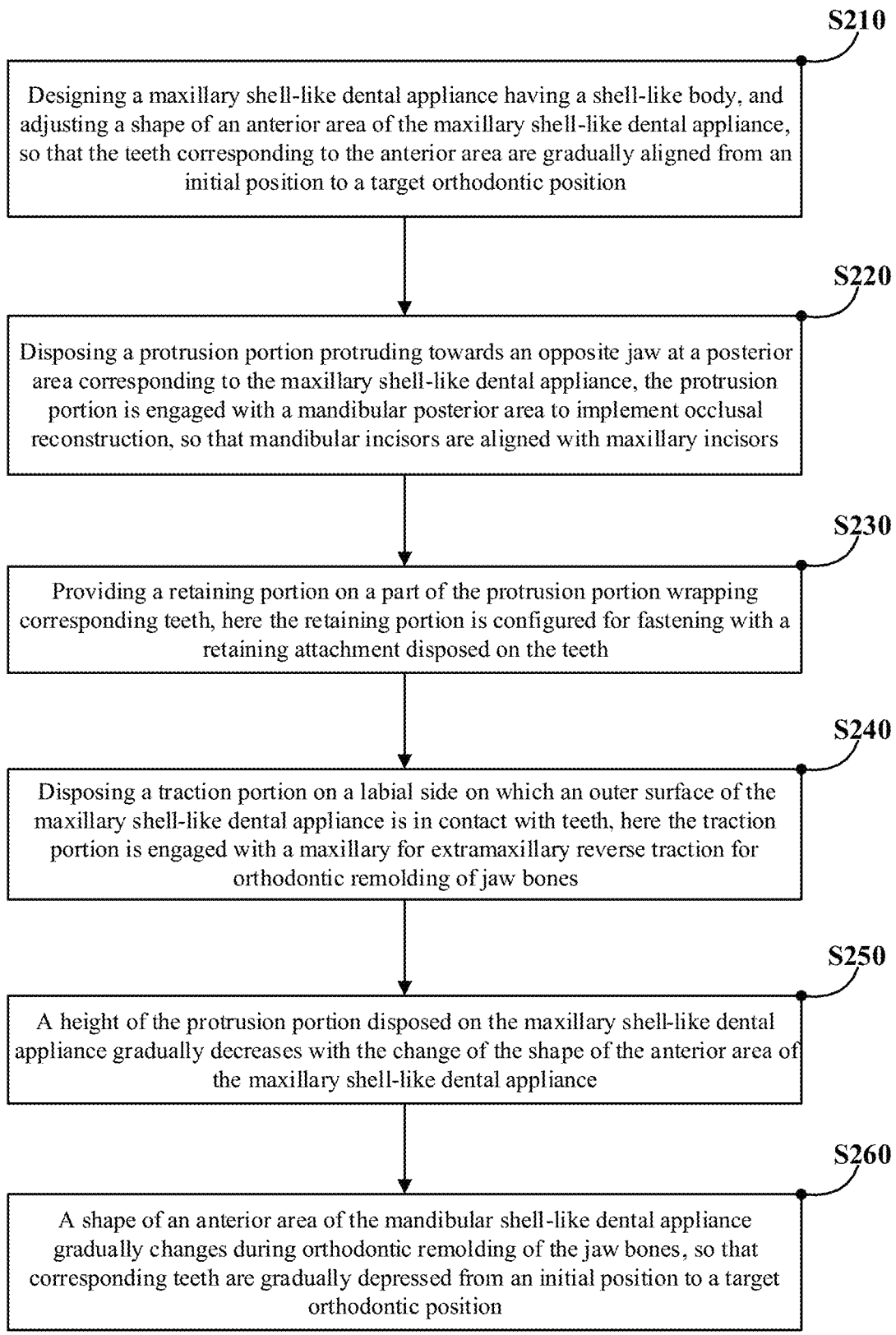
FIG. 13 is a flowchart of a design method for a mandibular positioning facial retrognathism orthodontic system in some embodiments of the present disclosure.

In addition, some embodiments of the present disclosure further provide a design method for a mandibular positioning facial retrognathism orthodontic system. FIG. 13 is a flowchart of a design method for the mandibular positioning facial retrognathism orthodontic system in the foregoing some embodiments. With reference to FIG. 1 to FIG. 5, the design method includes the following steps.

S210: Designing a maxillary shell-like dental appliance 1 having a shell-like body 11, and adjusting a shape of an anterior area of the maxillary shell-like dental appliance 1, so that the teeth corresponding to the anterior area are gradually aligned from an initial position to a target orthodontic position.

S220: Disposing a protrusion portion 12 protruding towards an opposite jaw at a posterior area corresponding to the maxillary shell-like dental appliance 1, here the protrusion portion 12 is engaged with a mandibular posterior area to implement occlusal reconstruction, so that mandibular incisors are aligned with maxillary incisors.

S230: Providing a retaining portion 13 on a part of the protrusion portion 12 wrapping corresponding teeth, here the retaining portion 13 is configured for fastening with a retaining attachment disposed on the teeth.

S240: Disposing a traction portion 14 on a labial side on which an outer surface of the maxillary shell-like dental appliance 1 is in contact with teeth, here the traction portion 14 is engaged with a maxillary for extramaxillary reverse traction for orthodontic remolding of jaw bones.

S250: A height of the protrusion portion 12 disposed on the maxillary shell-like dental appliance 1 gradually decreases with the change of the shape of the anterior area of the maxillary shell-like dental appliance 1.

S260: A shape of an anterior area of the mandibular shell-like dental appliance 1 gradually changes during orthodontic remolding of the jaw bones, so that corresponding teeth are gradually depressed from an initial position to a target orthodontic position.

In some embodiments, the shell-like dental appliances are worn in both the upper and lower jaws, to implement simultaneous orthodontic of the upper and lower jaws. Specifically, when the upper jaw simultaneously undergoes the jaw bone orthopedics and the dental orthodontic, and the mandibular shell-like dental appliance 2 also performs orthodontic on the mandibular teeth.

Figure 14:
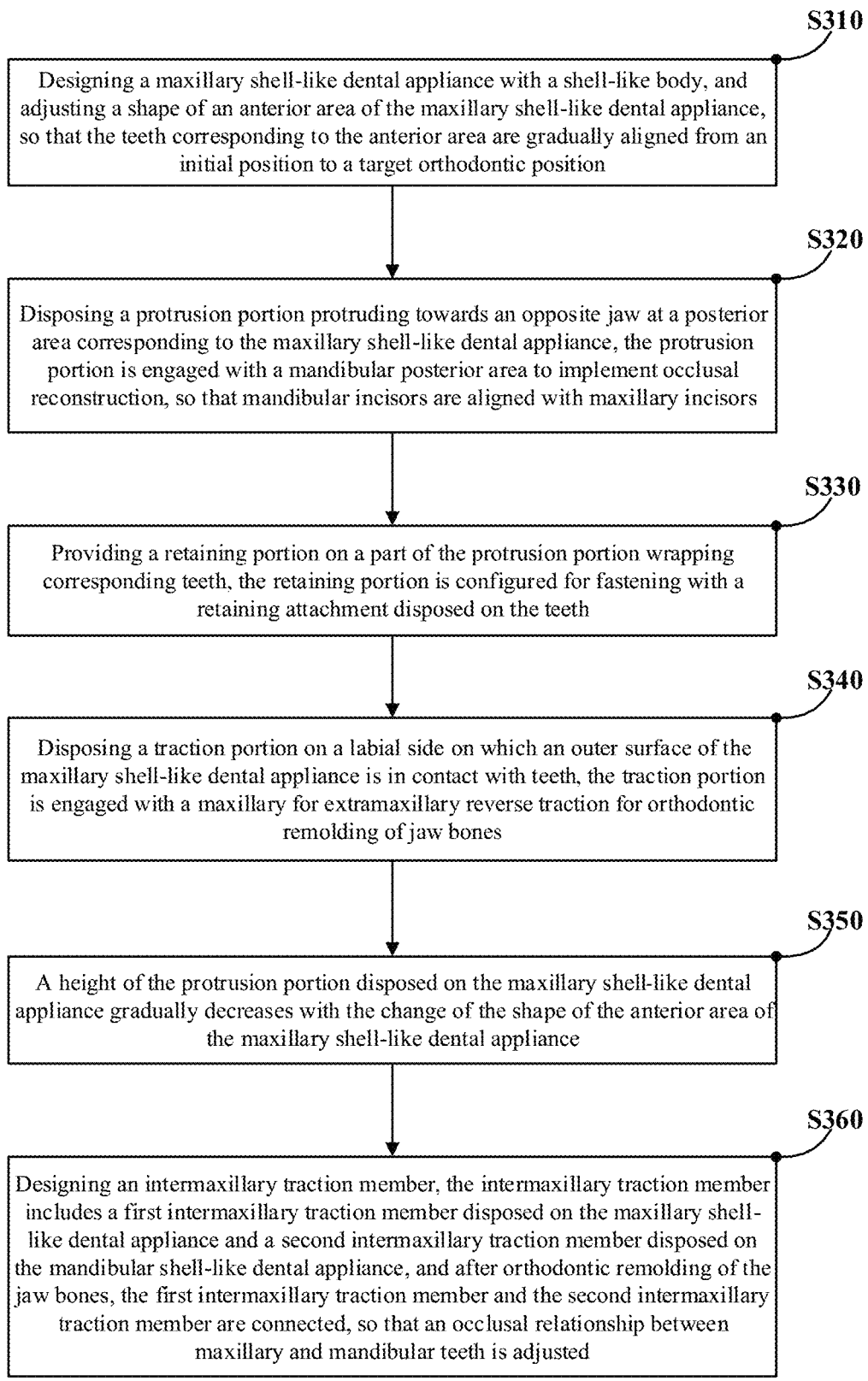
FIG. 14 is a flowchart of another design method for a mandibular positioning facial retrognathism orthodontic system in some embodiments of the present disclosure.

In addition, some embodiments of the present disclosure further provide a design method for a mandibular positioning facial retrognathism orthodontic system. FIG. 14 is a flowchart of a design method for the mandibular positioning facial retrognathism orthodontic system provided in the foregoing some embodiments. With reference to FIG. 1 to FIG. 6, the design method includes the following steps.

S310: Designing a maxillary shell-like dental appliance 1 with a shell-like body 11, and adjusting a shape of an anterior area of the maxillary shell-like dental appliance 1, so that the teeth corresponding to the anterior area are gradually aligned from an initial position to a target orthodontic position.

S320: Disposing a protrusion portion 12 protruding towards an opposite jaw at a posterior area corresponding to the maxillary shell-like dental appliance 1, here the protrusion portion 12 is engaged with a mandibular posterior area to implement occlusal reconstruction, so that mandibular incisors are aligned with maxillary incisors.

S330: Providing a retaining portion 13 on a part of the protrusion portion 12 wrapping corresponding teeth, here the retaining portion 13 is configured for fastening with a retaining attachment disposed on the teeth.

S340: Disposing a traction portion 14 on a labial side on which an outer surface of the maxillary shell-like dental appliance 1 is in contact with teeth, here the traction portion 14 is engaged with a maxillary for extramaxillary reverse traction for orthodontic remolding of jaw bones.

S350: A height of the protrusion portion 12 disposed on the maxillary shell-like dental appliance 1 gradually decreases with the change of the shape of the anterior area of the maxillary shell-like dental appliance 1.

S360: Designing an intermaxillary traction member, here the intermaxillary traction member includes a first intermaxillary traction member 31 disposed on the maxillary shell-like dental appliance 1 and a second intermaxillary traction member 32 disposed on the mandibular shell-like dental appliance 2, and after orthodontic remolding of the jaw bones, the first intermaxillary traction member 31 and the second intermaxillary traction member 32 are connected, so that an occlusal relationship between maxillary and mandibular teeth is adjusted.

A first intermaxillary traction member 31 is disposed on the maxillary shell-like dental appliance 1 and a second intermaxillary traction member 32 is disposed on the mandibular shell-like dental appliance 2, and after orthodontic remolding of the jaw bones, the first intermaxillary traction member 31 and the second intermaxillary traction member 32 are connected by an elastic member 33, so that an occlusal relationship between maxillary and mandibular teeth is adjusted. Specifically, through orthodontic remolding of the bones of the maxillary shell-like dental appliance 1 provided in FIG. 3 and FIG. 4, and using an occlusal fine adjustment as a main objective, class III intermaxillary traction may be performed by using the first intermaxillary traction member 31 and the second intermaxillary traction member 32, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class III intermaxillary traction. The posterior teeth of the mandibular dentition may further be moved further according to orthodontic requirements, to better implement the overall adduction of the mandibular dentition and implement the maxillary and mandibular occlusal fine adjustment.

Figure 15:
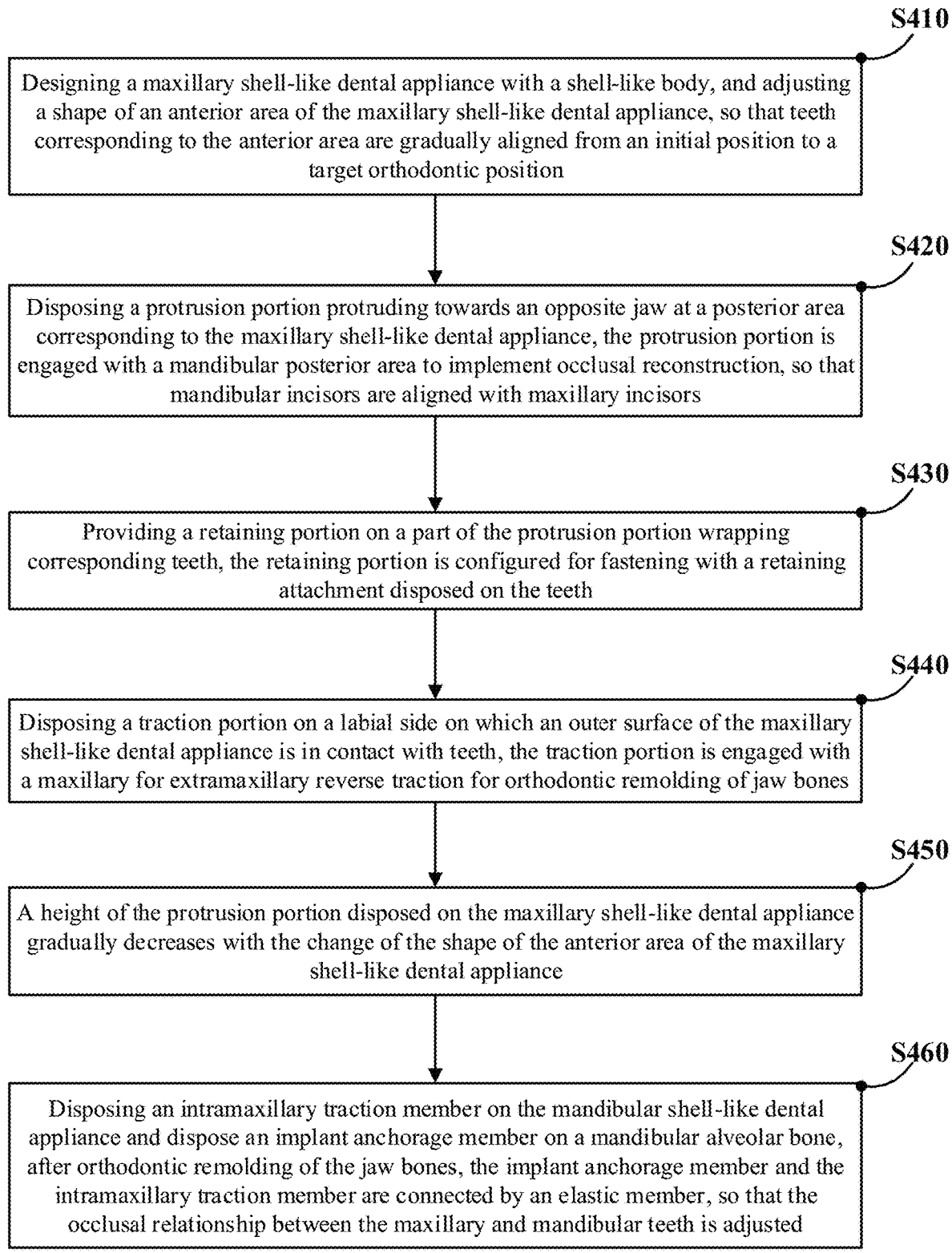
FIG. 15 is a flowchart of another design method for a mandibular positioning facial retrognathism orthodontic system in some embodiments of the present disclosure.

In addition, some embodiments of the present disclosure further provide a design method for a mandibular positioning facial retrognathism orthodontic system. FIG. 15 is a flowchart of a design method for the mandibular positioning facial retrognathism orthodontic system provided in the foregoing some embodiments. With reference to FIG. 1 to FIG. 5, and FIG. 7, the design method includes the following steps.

S410: Designing a maxillary shell-like dental appliance 1 with a shell-like body, and adjusting a shape of an anterior area of the maxillary shell-like dental appliance 1, so that teeth corresponding to the anterior area are gradually aligned from an initial position to a target orthodontic position.

S420: Disposing a protrusion portion 12 protruding towards an opposite jaw at a posterior area corresponding to the maxillary shell-like dental appliance 1, here the protrusion portion 12 is engaged with a mandibular posterior area to implement occlusal reconstruction, so that mandibular incisors are aligned with maxillary incisors.

S430: Providing a retaining portion 13 on a part of the protrusion portion 12 wrapping corresponding teeth, here the retaining portion 13 is configured for fastening with a retaining attachment disposed on the teeth.

S440: Disposing a traction portion 14 on a labial side on which an outer surface of the maxillary shell-like dental appliance 1 is in contact with teeth, here the traction portion 14 is engaged with a maxillary for extramaxillary reverse traction for orthodontic remolding of jaw bones.

S450: A height of the protrusion portion 12 disposed on the maxillary shell-like dental appliance 1 gradually decreases with the change of the shape of the anterior area of the maxillary shell-like dental appliance 1.

S460: Disposing an intramaxillary traction member on the mandibular shell-like dental appliance 2 and dispose an implant anchorage member 51 on a mandibular alveolar bone, here after orthodontic remolding of the jaw bones, the implant anchorage member 51 and the intramaxillary traction member 52 are connected by an elastic member 53, so that the occlusal relationship between the maxillary and mandibular teeth is adjusted.

After orthodontic remolding of the bones is completed for the upper and lower jaws, and an occlusal fine adjustment is used as a main objective, class I intramaxillary traction may be performed by using the intramaxillary traction member 52, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class I intramaxillary traction. Specifically, an intramaxillary traction member 52 disposed on the mandibular shell-like dental appliance 2 and an implant anchorage member 51 disposed on a mandibular alveolar bone, and after orthodontic remolding of the jaw bones, the implant anchorage member 51 and the intramaxillary traction member 52 are connected by an elastic member 53, so that the occlusal relationship between the maxillary and mandibular teeth is adjusted.

Figure 16:
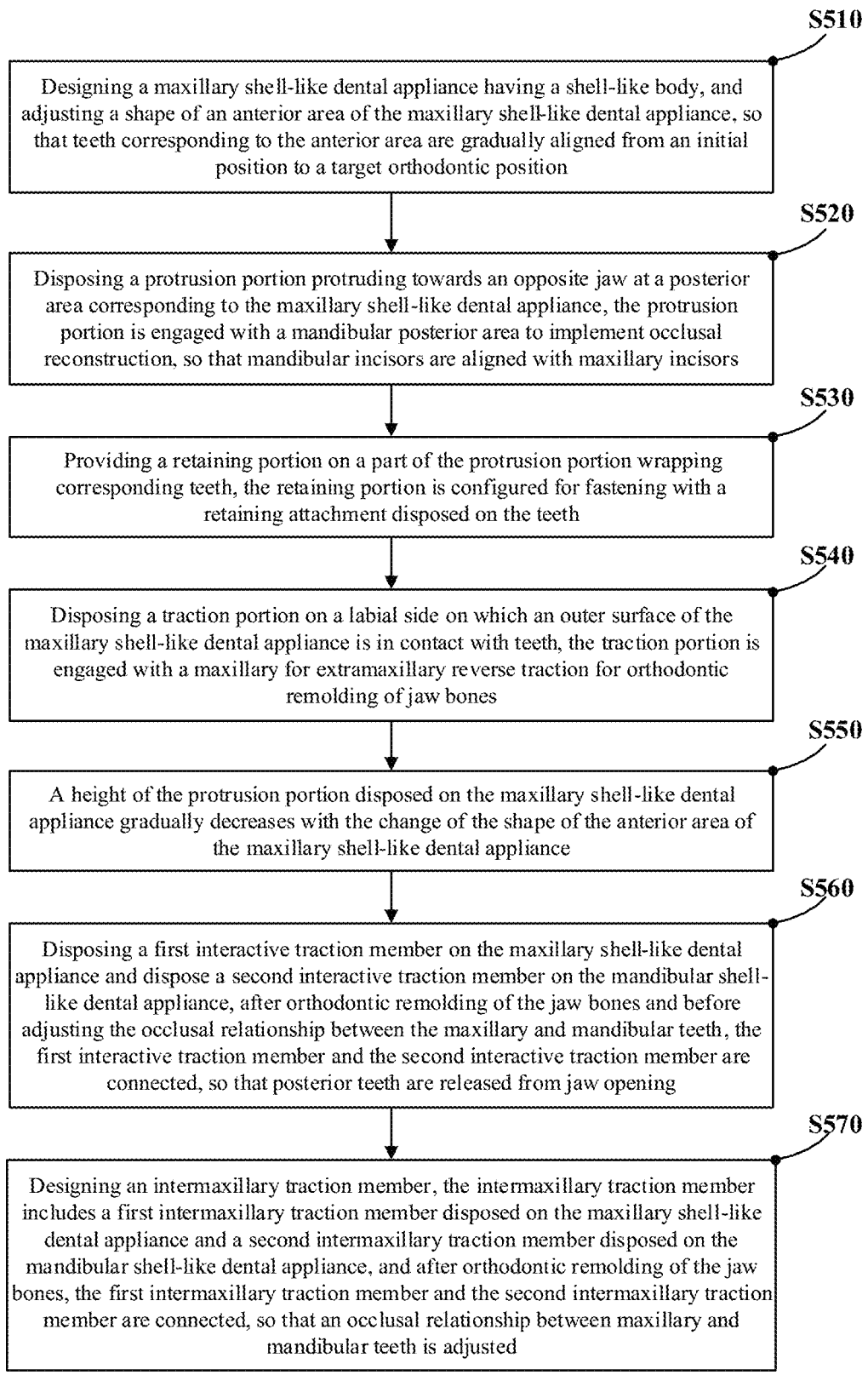
FIG. 16 is a flowchart of another design method for a mandibular positioning facial retrognathism orthodontic system in some embodiments of the present disclosure.

In addition, some embodiments of the present disclosure further provide a design method for a mandibular positioning facial retrognathism orthodontic system. FIG. 16 is a flowchart of a design method for the mandibular positioning facial retrognathism orthodontic system provided in the foregoing some embodiments. With reference to FIG. 1 to FIG. 4, FIG. 6, and FIG. 8 to FIG. 10, the design method includes the following steps.

S510: Designing a maxillary shell-like dental appliance 1 having a shell-like body, and adjusting a shape of an anterior area of the maxillary shell-like dental appliance 1, so that teeth corresponding to the anterior area are gradually aligned from an initial position to a target orthodontic position.

S520: Disposing a protrusion portion 12 protruding towards an opposite jaw at a posterior area corresponding to the maxillary shell-like dental appliance 1, here the protrusion portion 12 is engaged with a mandibular posterior area to implement occlusal reconstruction, so that mandibular incisors are aligned with maxillary incisors.

S530: Providing a retaining portion 13 on a part of the protrusion portion 12 wrapping corresponding teeth, here the retaining portion 13 is configured for fastening with a retaining attachment disposed on the teeth.

S540: Disposing a traction portion 14 on a labial side on which an outer surface of the maxillary shell-like dental appliance 1 is in contact with teeth, here the traction portion 14 is engaged with a maxillary for extramaxillary reverse traction for orthodontic remolding of jaw bones.

S550: A height of the protrusion portion 12 disposed on the maxillary shell-like dental appliance 1 gradually decreases with the change of the shape of the anterior area of the maxillary shell-like dental appliance 1.

S560: Disposing a first interactive traction member 41 on the maxillary shell-like dental appliance 1 and dispose a second interactive traction member 42 on the mandibular shell-like dental appliance 2, here after orthodontic remolding of the jaw bones and before adjusting the occlusal relationship between the maxillary and mandibular teeth, the first interactive traction member 41 and the second interactive traction member 42 are connected, so that posterior teeth are released from jaw opening.

S570: Designing an intermaxillary traction member, here the intermaxillary traction member includes a first intermaxillary traction member 31 disposed on the maxillary shell-like dental appliance 1 and a second intermaxillary traction member 32 disposed on the mandibular shell-like dental appliance 2, and after orthodontic remolding of the jaw bones, the first intermaxillary traction member 31 and the second intermaxillary traction member 32 are connected, so that an occlusal relationship between maxillary and mandibular teeth is adjusted.

Compared with the foregoing some embodiments, a main objective is to release posterior teeth from jaw opening. If the jaw opening is relatively large, the design method for a mandibular positioning facial retrognathism orthodontic system may further be designed with upper and lower interactive traction.

A first intermaxillary traction member 41 is disposed on the maxillary shell-like dental appliance 1 and a second intermaxillary traction member 42 is disposed on the mandibular shell-like dental appliance 2, and after orthodontic remolding of the jaw bones, the first intermaxillary traction member 41 and the second intermaxillary traction member 42 are connected by an elastic member 43, so that an occlusal relationship between maxillary and mandibular teeth is adjusted. Specifically, through orthodontic remolding of the bones of the maxillary shell-like dental appliance 1, and using an occlusal fine adjustment as a main objective, class III intermaxillary traction may be performed by using the intermaxillary traction member, and an attachment of the maxillary and mandibular dentition may be replaced according to orthodontic requirements. That is, the retaining attachment is removed from the teeth, and is replaced with an attachment suitable for the occlusal fine adjustment, for example, a traction member for class III intermaxillary traction. The posterior teeth of the mandibular dentition may further be moved further according to orthodontic requirements, to better implement the overall adduction of the mandibular dentition and implement the maxillary and mandibular occlusal fine adjustment.

The specific examples are used above to describe the present disclosure, are only used for helping understand the present disclosure, but are not intended to limit the present disclosure. A person skilled in the art to which the present disclosure belongs may further make several simple deductions, modifications, or substitutions according to the idea of the present disclosure.

What is claimed is:

1. A mandibular positioning facial retrognathism orthodontic system, comprising:
 a maxillary shell-like dental appliance having a plurality of shell-like bodies;
 wherein each of the plurality of shell-like bodies of the maxillary shell-like dental appliance is provided with a plurality of cavities for accommodating teeth, a protrusion portion protruding toward an opposite jaw is disposed at a posterior area corresponding to each of the plurality of shell-like bodies of the maxillary shell-like dental appliance, a traction portion is disposed at a labial side of each of the plurality of shell-like bodies of the maxillary shell-like dental appliance, and a retaining portion is disposed at the posterior area corresponding to each of the plurality of shell-like bodies of the maxillary shell-like dental appliance, wherein the retaining portion is configured for fastening with a retaining attachment;

the protrusion portion is configured to engage with the posterior area of a mandible to open occlusion of a patient for occlusal reconstruction, so that mandibular incisors are aligned with maxillary incisors; the traction portion is configured for drawing an upper jaw for orthodontic remolding of jaw bones towards the outside of the mouth; and the plurality of shell-like bodies of the maxillary shell-like dental appliance are configured to gradually change a shape of an anterior area of the maxillary shell-like dental appliance, so that corresponding teeth are gradually aligned from an initial position to a target orthodontic position, and a height, measured from an occlusal line of the teeth, of the protrusion portion disposed on the maxillary shell-like dental appliance gradually decreases with the change of the shape of the anterior area of the maxillary shell-like dental appliance, wherein the mandibular positioning facial retrognathism orthodontic system further comprises a mandibular shell-like dental appliance, the mandibular shell-like dental appliance comprises a plurality of shell-like bodies each provided with a plurality of cavities for accommodating mandibular teeth, and the plurality of shell-like bodies of the mandibular shell-like dental appliance are configured to gradually change a shape of an anterior area of the mandibular shell-like dental appliance during orthodontic remolding of the jaw bones, so that corresponding teeth are gradually depressed from an initial position to a target orthodontic position, wherein the mandibular positioning facial retrognathism orthodontic system further comprises a first intermaxillary traction member disposed on one of the plurality of shell-like bodies of the maxillary shell-like dental appliance and a second intermaxillary traction member disposed on one of the plurality of shell-like bodies of the mandibular shell-like dental appliance, and after orthodontic remolding of the jaw bones, the first intermaxillary traction member and the second intermaxillary traction member are connected by an elastic member, so that an occlusal relationship between maxillary and mandibular teeth is adjusted, wherein the mandibular positioning facial retrognathism orthodontic system further comprises a first interactive traction member disposed on one of the plurality of shell-like bodies of the maxillary shell-like dental appliance and a second interactive traction member disposed on one of the plurality of shell-like bodies of the mandibular shell-like dental appliance, the first interactive traction member and the second interactive traction member are respectively disposed on a buccal side and a labial side of the upper and lower jaws, or are respectively disposed on a labial side or a buccal side of the upper and lower jaws, and after orthodontic remolding of the jaw bones and before adjusting the occlusal relationship between the maxillary and mandibular teeth, the first interactive traction member and the second interactive traction member are connected by an elastic member, so that posterior teeth are released from jaw opening.

2. The mandibular positioning facial retrognathism orthodontic system according to claim 1, wherein the plurality of shell-like bodies of the mandibular shell-like dental appliance are further configured to gradually change a shape of a posterior area of the mandibular shell-like dental appliance, so that corresponding teeth are gradually adducted from the initial position to the target orthodontic position.

3. The mandibular positioning facial retrognathism orthodontic system according to claim 1, wherein the mandibular positioning facial retrognathism orthodontic system further comprises an intramaxillary traction member disposed on one of the plurality of shell-like bodies of the mandibular shell-like dental appliance and an implant anchorage member disposed on a mandibular alveolar bone, and after orthodontic remolding of the jaw bones, the implant anchorage member and the intramaxillary traction member are connected by an elastic member, so that the occlusal relationship between the maxillary and mandibular teeth is adjusted.

4. The mandibular positioning facial retrognathism orthodontic system according to claim 1, wherein a part of the protrusion portion facing an opposing jaw dentition occlusal surface is provided with a friction portion configured to provide a stable contact between upper and lower jaws during occlusal reconstruction.

5. The mandibular positioning facial retrognathism orthodontic system according to claim 4, wherein the friction portion is of one, two or a combination of more than two of a structure for concave-convex engagement with an opposing tooth occlusal surface, a structure for occlusal engagement with the opposing tooth occlusal surface, a structure with a matte surface, a structure with bumps, a structure with a hollowed surface, or a structure with a porous surface.

6. The mandibular positioning facial retrognathism orthodontic system according to claim 1, wherein the retaining portion has at least two outer surfaces, and each of the outer surfaces of the retaining portion is disposed at a specific angle relative to a labial side of the maxillary shell-like dental appliance.

7. The mandibular positioning facial retrognathism orthodontic system according to claim 6, wherein the retaining portion comprises a first curved surface and a second curved surface, the first curved surface and the second curved surface jointly define a retaining attachment accommodating space having an open end and a closed end, bending directions of the first curved surface and the second curved surface are the same, and curvatures of the first curved surface and the second curved surface are different.

8. The mandibular positioning facial retrognathism orthodontic system according to claim 7, wherein an included angle formed between a tangential direction at any point on the first curved surface and a tangential direction at any point on the second curved surface is an acute angle.

9. A design method for a mandibular positioning facial retrognathism orthodontic system, comprising steps of:

designing a maxillary shell-like dental appliance having a plurality of shell-like bodies configured to adjust a shape of an anterior area of the maxillary shell-like dental appliance, so that teeth corresponding to the anterior area are gradually aligned from an initial position to a target orthodontic position;

disposing a protrusion portion protruding towards an opposite jaw at a posterior area corresponding to each of the plurality of shell-like bodies of the maxillary shell-like dental appliance, wherein the protrusion portion is configured to engage with a mandibular posterior area to open occlusion of a patient for occlusal reconstruction, so that mandibular incisors are aligned with maxillary incisors;

providing a retaining portion on a part of the protrusion portion wrapping corresponding teeth, wherein the retaining portion is configured for fastening with a retaining attachment disposed on the teeth;

disposing a traction portion on a labial side of each of the plurality of shell-like bodies of the maxillary shell-like dental appliance, wherein the traction portion is configured for drawing an upper jaw for orthodontic remolding of jaw bones towards the outside of the mouth, wherein a height, measured from an occlusal line of the teeth, of the protrusion portion disposed on the maxillary shell-like dental appliance gradually decreases with a change of the shape of the anterior area of the maxillary shell-like dental appliance;

designing a mandibular shell-like dental appliance comprising a plurality of shell-like bodies each provided with a plurality of cavities for accommodating mandibular teeth, wherein the plurality of shell-like bodies of the mandibular shell-like dental appliance are configured to gradually change a shape of an anterior area of the mandibular shell-like dental appliance during orthodontic remolding of the jaw bones, so that corresponding teeth are gradually depressed from an initial position to a target orthodontic position;

disposing a first intermaxillary traction member on one of the plurality of shell-like bodies of the maxillary shell-like dental appliance and a second intermaxillary traction member disposed on one of the plurality of shell-like bodies of the mandibular shell-like dental appliance, wherein after orthodontic remolding of the jaw bones, the first intermaxillary traction member and the second intermaxillary traction member are connected by an elastic member, so that an occlusal relationship between maxillary and mandibular teeth is adjusted; and disposing a first interactive traction member on one of the plurality of shell-like bodies of the maxillary shell-like dental appliance and a second interactive traction member disposed on one of the plurality of shell-like bodies of the mandibular shell-like dental appliance, wherein the first interactive traction member and the second interactive traction member are respectively disposed on a buccal side and a labial side of the upper and lower jaws, or are respectively disposed on a labial side or a buccal side of the upper and lower jaws, and after orthodontic remolding of the jaw bones and before adjusting the occlusal relationship between the maxillary and mandibular teeth, the first interactive traction member and the second interactive traction member are connected by an elastic member, so that posterior teeth are released from jaw opening.

10. The design method for a mandibular positioning facial retrognathism orthodontic system according to claim 9, wherein the plurality of shell-like bodies of the mandibular shell-like dental appliance are further configured to gradually change a shape of a posterior area of the mandibular shell-like dental appliance, so that corresponding teeth are gradually adducted from the initial position to the target orthodontic position.

11. The design method for a mandibular positioning facial retrognathism orthodontic system according to claim 9, wherein the design method further comprises: disposing an intramaxillary traction member on one of the plurality of shell-like bodies of the mandibular shell-like dental appliance and disposing an implant anchorage member on a mandibular alveolar bone, wherein after orthodontic remolding of the jaw bones, the implant anchorage member and the intramaxillary traction member are connected by an elastic member, so that the occlusal relationship between the maxillary and mandibular teeth is adjusted.

\* \* \* \* \*